(12) United States Patent
Moreau et al.

(10) Patent No.: US 8,129,432 B2
(45) Date of Patent: Mar. 6, 2012

(54) METHOD OF CORRECTING IMBALANCE BETWEEN BONE RESORPTION AND BONE FORMATION AND KITS AND COMPOSITIONS THEREFOR

(75) Inventors: Alain Moreau, Montreal (CA); Genevieve Mailhot, Outremont (CA)

(73) Assignee: CHU Sainte-Justine, Montreal (CA)

(*) Notice: Subject to any disclaimer, the term of this patent is extended or adjusted under 35 U.S.C. 154(b) by 231 days.

(21) Appl. No.: 12/526,311

(22) PCT Filed: Feb. 15, 2008

(86) PCT No.: PCT/CA2008/000312
§ 371 (c)(1),
(2), (4) Date: Aug. 7, 2009

(87) PCT Pub. No.: WO2008/098379
PCT Pub. Date: Aug. 21, 2008

(65) Prior Publication Data
US 2010/0029567 A1 Feb. 4, 2010

Related U.S. Application Data

(60) Provisional application No. 60/890,100, filed on Feb. 15, 2007, provisional application No. 60/912,267, filed on Apr. 17, 2007, provisional application No. 60/915,196, filed on May 1, 2007, provisional application No. 60/938,025, filed on May 15, 2007.

(51) Int. Cl.
*A61K 31/165* (2006.01)
*A61K 31/16* (2006.01)

(52) U.S. Cl. .................................. 514/629; 514/613

(58) Field of Classification Search .................. None
See application file for complete search history.

(56) References Cited

U.S. PATENT DOCUMENTS

| | | |
|---|---|---|
| 5,071,875 A | 12/1991 | Horn et al. |
| 5,151,446 A | 9/1992 | Horn et al. |
| 5,434,183 A | 7/1995 | Larsson-Backström |
| 5,856,124 A | 1/1999 | Reppert et al. |
| 6,143,789 A | 11/2000 | Lefoulon et al. |
| 7,365,209 B2 | 4/2008 | Letourneau et al. |
| 2005/0019841 A1 | 1/2005 | Garman et al. |

FOREIGN PATENT DOCUMENTS

| | | |
|---|---|---|
| EP | 0919541 | 11/1998 |
| WO | WO 2004/040000 A2 | 5/2004 |
| WO | WO 2005/078444 A1 | 8/2005 |
| WO | WO 2005/078455 | 8/2005 |

OTHER PUBLICATIONS

Delmas et al., "Effects of Raloxifene on Bone Mineral Density, Serum Cholesterol Concentrations, and Uterine Endometrium in Postmenopausal Women," *J of Med.*, 337(23):1641-1647, 1997.

Ma et al., "New Bone Formation with Teriparatide [Human Parathyroid Hormone-(1-34)] Is Not Retarded by Long-Term Pretreatment with Alendronate, Estrogen, or Raloxifene in Ovariectomized Rats," *Endocrinology*, 144(5):2008-2015, 2003.

Mahmood, et al., "Selection of the First-Time Dose in Humans: Comparison of Different Approaches Based on Interspecies Scaling of Clearance," *J Clin Pharmacol.*, 43:692-697, 2003.

Roth et al., "Melatonin promotes osteoblast differentiation and bone formation," *J Bio Chem.*, 274(45):22041-22047, 1999.

Saudek et al., "A preliminary trial of the programmable implantable medication system for insulin delivery," *N Engl J Med*, 321:574-579, 1989.

Witt-Enderby et al., "Therapeutic treatments potentially mediated by melatonin receptors: potential clinical uses in the prevention of osteoporosis, cancer and as an adjuvant therapy," *J. Pineal Res.*, 41:297-305, 2006.

Supplemental European Search Report, European Application No. EP 08714635, 4 pages, Mar. 17, 2010.

European Communication pursuant to Article 94(3) EPC, dated Jun. 29, 2010, 1 page.

*Primary Examiner* — David Romeo
(74) *Attorney, Agent, or Firm* — Klarquist Sparkman, LLP.

(57) ABSTRACT

Compounds, methods, uses, compositions, kits and packages for the treatment of imbalance between bone resorption and bone formation, based on uses of 4-phenyl-2 propionamidotetralin (4-P-PDOT) and analogs, derivatives, prodrugs, precursors thereof, and salts thereof, are described.

15 Claims, 32 Drawing Sheets

A

B

|  | | Mouse 583 Right Femur | | Mouse 590 Right Femur | | Units |
|---|---|---|---|---|---|---|
|  | | Treatment: 4PPDOT | | Treatment: Vehicule | | |
|  | | A-253-Goldner | A-253-TRAP | A-283-Goldner | A-283-TRAP | |
| % Bone Volume / Tissue Volume | BV/TV | 18,2 | 15,4 | 8,8 | 10,1 | % |
| Trabecular Thickness | Tb.Th | 44 | 32 | 25 | 30 | mcm |
| Trabecular Number | Tb.N | 4,1 | 4,8 | 3,5 | 3,4 | /mm |
|  | | Total Osteoclasts | Actives Osteoclasts | Total Osteoclasts | Actives Osteoclasts | |
| % Osteoclast Surface / Bone Surface | Oc.S/BS | 11,3 | 1,8 | 9,4 | 5,4 | % |
| Osteoclasts per mm B.Pm | N.Oc/B.Pm | 4,9 | 0,9 | 2,3 | 2,6 | /mm |

Figure 21

SEQUENCE LISTING

<160> NUMBER OF SEQ ID NOS: 4

<210> SEQ ID NO 1
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1

```
gcaggtaatt tgtttgtggt                                              20

<210> SEQ ID NO 2
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 2
agatgcgtgg atcatactct                                              20

<210> SEQ ID NO 3
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 3
tgtaccgcaa caagaagctc agga                                         24

<210> SEQ ID NO 4
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 4
tggcgatgag tgtcagcatc cata                                         24
```

METHOD OF CORRECTING IMBALANCE BETWEEN BONE RESORPTION AND BONE FORMATION AND KITS AND COMPOSITIONS THEREFOR

CROSS REFERENCE TO RELATED APPLICATIONS

This is the U.S. National Stage of PCT application No. PCT/CA2008/000312 filed on Feb. 15, 2008 and published in English under PCT Article 21(2), which itself claims the benefit of U.S. provisional application Ser. No. 60/890,100, filed on Feb. 15, 2007, of U.S. provisional application Ser. No. 60/912,267, filed on Apr. 17, 2007, of U.S. provisional application Ser. No. 60/915,196 filed on May 1, 2007 and of U.S. provisional application Ser. No. 60/938,025 filed on May 15, 2007. The contents of the above documents are incorporated herein by reference in their entirety.

STATEMENT REGARDING FEDERALLY SPONSORED RESEARCH OR DEVELOPMENT

N/A.

FIELD OF THE INVENTION

The present invention relates to methods of correcting imbalance between bone resorption and bone formation, and kits and compositions therefor.

SEQUENCE LISTING

This application contains a Sequence Listing in computer readable form entitled 14033$_{-33}$—sequence listing$_{-ST}$25, created Feb. 14, 2008 having a size of 2Ko. The computer readable form is incorporated herein by reference.

BACKGROUND OF THE INVENTION

Bones undergo a process of constant remodeling consisting of the breakdown of old bone and re-building of new bone. This resorption (by osteoclasts) and formation (by osteoblasts) occurs at an approximately equal rate thereby maintaining strength of the entire skeleton. Bone remodeling enables the renewal of bone mass and is subjected to the influence of a number of hormones and growth factors. It has been shown that melatonin stimulates bone formation through its action on osteoblasts.

Osteoporosis is defined by the World Health Organization (WHO) in women as a bone mineral density 2.5 standard deviations below peak bone mass (20-year-old sex-matched healthy person average) as measured by dual energy X-ray absorptiometry (DXA); the term "established osteoporosis" includes the presence of a fragility fracture.

There are two types of osteoporosis: (1) Primary osteoporosis—bone loss that occurs as a consequence of the normal aging process and most often affects postmenopausal women and (2) Secondary osteoporosis—bone loss that occurs as a consequence of other factors such as a chronic medical condition, nutritional deficiency, or certain types of medications.

Currently, in the United States, several medications are approved by the U.S. Food and Drug Administration (FDA) for the prevention and treatment of osteoporosis and are considered as first-line medications. These medications include bisphosphonates, raloxifene, nasal calcitonin and teriparatide.

While treatment modalities are becoming available (such as the bisphosphonates), prevention is still considered the most efficient way to reduce fracture.

Accordingly, there is a need for novel methods for preventing and/or treating bone diseases such as osteoporosis.

The present description refers to a number of documents, the content of which is herein incorporated by reference in their entirety.

SUMMARY OF THE INVENTION

The present invention relates to methods of correcting imbalance between bone resorption and bone formation, and kits and compositions therefor.

More specifically, in accordance with an aspect of the present invention, there is provided a method comprising: (a) identifying a subject suffering from imbalance between bone resorption and bone formation; and (b) administering to said subject a therapeutically effective amount of (i) 4-phenyl-2-propionamidotetralin (4-P-PDOT); (ii) a derivative, analog, conjugate or prodrug of 4-P-PDOT; (iii) a pharmaceutical acceptable salt of (i) or (ii); or (iv) any combination of (i) to (iii), whereby imbalance between bone resorption and bone formation is corrected in said subject.

In an embodiment, the above-mentioned method comprises administering to said subject an effective amount of (i) 4-P-PDOT; (ii) a pharmaceutical acceptable salt of 4-P-PDOT; or (iii) any combination of (i) and (ii).

In an embodiment, the above-mentioned administration is a single bolus administration. In another embodiment, the above-mentioned administration is a daily administration.

In an embodiment, the above-mentioned therapeutically effective amount is between about 0.001 and about 500 mg/kg of subject/day.

In an embodiment, the above-mentioned method further comprises the administration of another agent selected from the group consisting of an MT2 melatonin receptor specific antagonist, a bisphosphonate, raloxifene, nasal calcitonin and teriparatide.

In another aspect, the present invention provides a kit or package comprising: (a) at least one compound selected from (i) 4-P-PDOT; (ii) a derivative, analog, conjugate or prodrug of 4-P-PDOT; and (iii) a pharmaceutical acceptable salt of (i) or (ii); and (b) instructions to administer said compound to a subject to correct or prevent bone mineralization defect.

In an embodiment, the above-mentioned kit or package comprises (i) 4-P-PDOT; (ii) a pharmaceutical acceptable salt of 4-P-PDOT; or (iii) any combination of (i) and (ii).

In an embodiment, the above-mentioned instructions are instructions to administer said compound to a subject to correct imbalance between bone resorption and bone formation.

In another embodiment, the above-mentioned kit or package further comprises another agent selected from the group consisting of a MT2 melatonin receptor specific antagonist, a bisphosphonate, raloxifene, nasal calcitonin and teriparatide.

In another aspect, the present invention provides a composition comprising: (a) (i) 4-P-PDOT; (ii) a derivative, analog, conjugate or prodrug of 4-P-PDOT; (iii) a pharmaceutical acceptable salt of (i) or (ii); or (iv) any combination of (i) to (iii); and (b) a therapeutically effective amount of an agent selected from the group consisting of a MT2 melatonin receptor specific antagonist, a bisphosphonate, raloxifene, nasal calcitonin and teriparatide.

In another aspect, the present invention provides a composition for correcting an imbalance between bone resorption and bone formation in a subject comprising: (a) (i) 4-P-PDOT; (ii) a derivative, analog, conjugate or prodrug of 4-P-

PDOT; (iii) a pharmaceutical acceptable salt of (i) or (ii); or (iv) any combination of (i) to (iii); and (b) a pharmaceutically acceptable carrier.

In another aspect, the present invention provides a bone targeted composition comprises: (a) (i) 4-P-PDOT; (ii) a derivative, analog, conjugate or prodrug of 4-P-PDOT; (iii) a pharmaceutical acceptable salt of (i) or (ii); or (iv) any combination of (i) to (iii); and (b) a pharmaceutically acceptable carrier.

In an embodiment, the above-mentioned composition comprises: (a) (i) 4-P-PDOT); (ii) a pharmaceutical acceptable salt of 4-P-PDOT; or (iii) any combination of (i) and (ii); and (b) a pharmaceutically acceptable carrier.

In another aspect, the present invention provides a use of a therapeutically effective amount of (i) 4-P-PDOT; (ii) a derivative, analog, conjugate or prodrug of 4-P-PDOT; (iii) a pharmaceutical acceptable salt of (i) or (ii); or (iv) any combination of (i) to (iii), in the manufacture of a medicament for the treatment of imbalance between bone resorption and bone formation.

In another aspect, the present invention provides a use of a therapeutically effective amount of (i) 4-P-PDOT; (ii) a derivative, analog, conjugate or prodrug of 4-P-PDOT; (iii) a pharmaceutical acceptable salt of (i) or (ii); or (iv) any combination of (i) to (iii), for the treatment of imbalance between bone resorption and bone formation.

In an embodiment, the above-mentioned use is of (i) 4-P-PDOT; (ii) a pharmaceutical acceptable salt of 4-P-PDOT; or (iii) a combination of (i) and (ii).

In an embodiment, the above-mentioned correction of imbalance between bone resorption and bone formation comprises at least one of: an inhibition of bone resorption; an inhibition of osteoclast differentiation; an increase in bone mineral density (BMD); an increase in bone mineral content (BMC); an increase of density of pure cortical bone; an increase of mean density of total bone; an increase of cortical thickness; an increase of pure cortical area assigned to be cortical; an increase of tibial diaphyseal total bone areas; an increase of mineralization apposition rate; an increase of bone formation rate/bone surface referent; an increase of mineralizing surface for endocortical or periosteal surface; a decrease of serum alkaline phosphatase; a decrease of intracortical regions of hypo-mineralized osteoid; a decrease of osteoid thickness and a decrease of osteoid condensation.

In a further embodiment, the above-mentioned correction of imbalance between bone resorption and bone formation comprises an inhibition of bone resorption. In another embodiment, the above-mentioned correction of imbalance between bone resorption and bone formation comprises an inhibition of osteoclast differentiation. In another embodiment, the above-mentioned correction of imbalance between bone resorption and bone formation comprises an increase in bone mineral density (BMD). In another embodiment, the above-mentioned correction of imbalance between bone resorption and bone formation comprises an increase in bone mineral content (BMC).

In an embodiment, the above-mentioned use further comprises the use of another agent selected from the group consisting of a MT2 melatonin receptor specific antagonist, a bisphosphonate, raloxifene, nasal calcitonin and teriparatide.

In another aspect, the present invention provides a method comprising: (a) identifying a subject suffering from imbalance between bone resorption and bone formation; and (b) administering a therapeutically effective amount of at least one MT2 melatonin receptor specific antagonist to the subject, whereby imbalance between bone resorption and bone formation is corrected in the subject.

In another aspect, the present invention provides a use of a therapeutically effective amount of at least one MT2 melatonin receptor specific antagonist in the manufacture of a medicament for the treatment of imbalance between bone resorption and bone formation.

In another aspect, the present invention provides a use of a therapeutically effective amount of at least one MT2 melatonin receptor specific antagonist in the treatment of imbalance between bone resorption and bone formation.

The present invention further provides a composition for the treatment of imbalance between bone resorption and bone formation, said composition comprising at least one MT2 melatonin receptor specific antagonist and a pharmaceutically acceptable carrier.

The present invention further provides a kit or package comprising at least one MT2 melatonin receptor specific antagonist and instructions for the treatment of imbalance between bone resorption and bone formation.

In an embodiment, the above-mentioned subject suffers from osteoporosis. In another embodiment, the above-mentioned subject suffers from Paget disease. In another embodiment, the above-mentioned subject suffers from osteolytic bone cancer. In another embodiment, the above-mentioned subject suffers from arthritis characterised by the presence of an inflammatory cytokine that induces osteoclasts.

In an embodiment, the above-mentioned subject is a mammal. In a further embodiment, the above-mentioned subject is a human.

As used herein the term "subject" is meant to refer to any mammal including human, mice, rat, dog, cat, pig, monkey, horse, etc. In a particular embodiment, it refers to a human.

The articles "a," "an" and "the" are used herein to refer to one or to more than one (i.e., to at least one) of the grammatical object of the article.

The term "including" and "comprising" are used herein to mean, and are used interchangeably with, the phrases "including but not limited to" and "comprising but not limited to".

The terms "such as" are used herein to mean, and are used interchangeably with, the phrase "such as but not limited to".

By "agonist" it is meant that the ligand stimulates a ligand-dependent receptor-characteristic activity above any baseline levels present in the absence of ligand. By "antagonist" it is meant that the ligand binds to the receptor and functions as a competitive or non-competitive inhibitor of receptor-characteristic agonist activity. By "inverse agonist" or "reverse agonist" it is meant that the ligand will bind to the receptor in question and cause the suppression of receptor activity lower than the amount of activity seen in the absence of receptor ligand. As used herein the terms "MT2 melatonin receptor specific antagonist" are meant to refer to an antagonist that binds specifically to the MT2 receptor as opposed to other antagonists which bind to other melatonin receptors such as luzindole.

As used herein the terms "osteoclast precursor" are meant to refer to a cell that is able to mature into an osteoclast. Without being so limited, such cell includes RAW264.7, spleen cells, haematopoietic cells able to mature into osteoclasts and $CD14^+$ monocytes.

There are a number of agents known to provoke the differentiation of an osteoclast precursor into an osteoclast. Without being so limited, they include Receptor Activator for Nuclear Factor Kappa B Ligand (RANKL), macrophage-colony stimulating factor (M-CSF), inflammatory cytokines such as tumor necrosis factor-alpha (TNF-α) and various interleukins able to stimulate osteoclast activity.

There are a number of resorbable bone analogs available commercially such as but not limited to BioCoat™. Other resorbable bone analogs include dentine fragment and hydroxyapatite.

There are a number of known animal models for imbalance between bone resorption and bone formation including C57Bl/6j mice, which is known to exhibit a very low bone mineral density (BMD), and osteoporosis animal models.

There are a number of known osteoporosis animal models including ovariectomized mice and rats.

Included within the scope of the subject invention are derivatives, analogs, conjugates, or prodrugs of 4-phenyl-2-propionamidotetralin (4-P-PDOT), and salts thereof, which have the ability, as described herein, to treat an imbalance between bone resorption and bone formation in a subject. The salt(s) mentioned herein include pharmaceutically acceptable salt(s). Various analogs, derivatives, conjugates and prodrugs of 4-P-PDOT are known and include, for example, 8-methoxy-2-propionamido-tetralin; 2-chloroacetamido-tetralin; 8-methoxy-2-n-butyramido-tetralin; 8-methoxy-2-cyclopropanecarbonylamido-tetralin; 8-methoxy-2-chloroacetamido-tetralin; 4-phenyl-2-acetamido-tetralin (4-P-ADOT); 4-benzyl-2-acetamidotetralin; 4-phenyl-2-chloroacetamido-tetralin (4-P-CADOT); and 4-benzyl-2-propionamido-tetralin, described in U.S. Pat. No. 5,071,875. In an embodiment, the above-mentioned derivative is 4-P-ADOT or 4-P-CADOT.

Kits

The present invention also relates to a kit or package for treating/preventing imbalance between bone resorption and bone formation (e.g. for inhibiting bone resorption or osteoclast maturation/differentiation) comprising at least one compound selected from (i) 4-phenyl-2-propionamidotetralin (4-P-PDOT); (ii) a derivative, analog, conjugate or prodrug of 4-P-PDOT; and (iii) a pharmaceutical acceptable salt of (i) or (ii); and instructions to administer said compound to a subject to inhibit inhibiting bone resorption or osteoclast maturation/differentiation. Such kits may also comprise a composition (e.g. a pharmaceutical composition) comprising at least one of the above-mentioned compounds and a pharmaceutically acceptable carrier. Such kits may further comprise at least one other active agent able to inhibit bone resorption or osteoclast maturation/differentiation. When the kit is used to inhibit bone resorption or osteoclast maturation/differentiation in a subject having osteoporosis, the kit may also further comprise at least one other active agent capable of preventing or correcting any other detrimental symptoms of osteoporosis. Such agents include without being so limited bisphosphonates, raloxifene, nasal calcitonin and teriparatide. In addition, a compartmentalized kit in accordance with the present invention includes any kit in which reagents are contained in separate containers. Such containers include small glass containers, plastic containers or strips of plastic or paper. Such containers allow the efficient transfer of reagents from one compartment to another compartment such that the samples and reagents are not cross-contaminated and the agents or solutions of each container can be added in a quantitative fashion from one compartment to another.

As used herein the term "imbalance between bone resorption and bone formation" is meant to refer to an increase in the rate of osteoclast maturation or differentiation, generating more mature osteoclasts as well as an increase of resorption activity by mature osteoclasts.

As used herein the term "correct" when used in the context of correction of an imbalance between bone resorption and bone formation is meant herein to refer to any partial or complete improvement of imbalance between bone resorption and bone formation. Such correction may correspond to, without being so limited, an inhibition of bone resorption, an inhibition of osteoclast differentiation, an increase in bone mineral density (BMD) and bone mineral content (BMC); an increase of density of pure cortical bone, an increase of mean density of total bone, an increase of cortical thickness, an increase of pure cortical area assigned to be cortical, an increase of tibial diaphyseal total bone areas, an increase of mineralization apposition rate, an increase of bone formation rate/bone surface referent, an increase of mineralizing surface for endocortical or periosteal surface; a decrease of serum alkaline phosphatase, a decrease of intra-cortical regions of hypo-mineralized osteoid, a decrease of osteoid thickness and a decrease of osteoid condensation.

Route of Administration

Pharmaceutical compositions of the present invention can be administered by routes such as orally, nasally, intravenously, intramuscularly, subcutaneously, sublingually, intrathecally, or intradermally. The route of administration can depend on a variety of factors, such as the environment and therapeutic goals.

By way of example, pharmaceutical composition of the invention can be in the form of a liquid, solution, suspension, pill, capsule, tablet, gelcap, powder, gel, ointment, cream, nebulae, mist, atomized vapor, aerosol, or phytosome. For oral administration, tablets or capsules can be prepared by conventional means with pharmaceutically acceptable excipients such as binding agents, fillers, lubricants, disintegrants, or wetting agents. The tablets can be coated by methods known in the art. Liquid preparations for oral administration can take the form of, for example, solutions, syrups, or suspension, or they can be presented as a dry product for constitution with saline or other suitable liquid vehicle before use. Dietary supplements of the invention also can contain pharmaceutically acceptable additives such as suspending agents, emulsifying agents, non-aqueous vehicles, preservatives, buffer salts, flavoring, coloring, and sweetening agents as appropriate. Preparations for oral administration also can be suitably formulated to give controlled release of the active ingredients.

Dosage

Any amount of a pharmaceutical composition can be administered to a subject. The dosages will depend on many factors including the mode of administration and the age of the subject. In younger people there is extensive bone-turnover due to growing bone. Typically, the amount of a compound or agent of the present invention (e.g., 4-P-PDOT, a derivative, analog, conjugate or prodrug of 4-P-PDOT; a pharmaceutical acceptable salt thereof) contained within a single dose will be an amount that effectively prevent, delay or correct bone resorption in a subject in need thereof without inducing significant toxicity. As used herein the term "therapeutically effective amount" is meant to refer to an amount effective to achieve the desired therapeutic effect. A therapeutically effective amount is also one in which any adverse side effects of the compound are outweighed by the therapeutically beneficial effects. Typically, a compound or agent of the present invention (e.g., 4-P-PDOT, a derivative, analog, conjugate or prodrug of 4-P-PDOT; or a pharmaceutical acceptable salt thereof) can be administered to subjects in doses ranging from 0.001 to 500 mg/kg/day and, in a more specific embodiment, 1 mg to 5 mg/kg/day. The allometric scaling method of Mahmood et al. (J. Clin. Pharmacol. 2003, 43(7): 692-7) can be used to extrapolate the dose from mice to human. Pharmaceutically acceptable preparations and salts of the small molecules of the present invention are within the scope of the present invention and are well known in the art (Remington's Pharmaceutical Science, $16^{th}$ Ed., Mack Ed.).

The dosage will be adapted by the clinician in accordance with conventional factors such as the extent of the disease and different parameters from the patient.

The therapeutically effective amount of a compound or agent of the present invention (e.g., 4-P-PDOT, a derivative, analog, conjugate or prodrug of 4-P-PDOT; or a pharmaceutical acceptable salt thereof) may also be measured directly. The effective amount may be given daily or weekly or fractions thereof. Typically, a pharmaceutical composition of the invention can be administered in an amount from about 0.001 mg up to about 500 mg per kg of body weight per day (e.g., 1 mg, 2 mg, 3 mg, 4 mg, 5 mg, 10 mg, 50 mg, 100 mg, or 250 mg). Dosages may be provided in either a single or multiple dosage regimen(s). For example, in some embodiments the effective amount is a dose that ranges from about 1 mg to about 25 grams of the agent per day, about 50 mg to about 10 grams of the agent per day, from about 100 mg to about 5 grams of the agent per day, about 1 gram of the agent per day, about 1 mg to about 25 grams of the agent per week, about 50 mg to about 10 grams of the agent per week, about 100 mg to about 5 grams of the agent every other day, and about 1 gram of the agent once a week.

These are simply guidelines since the actual dose must be carefully selected and titrated by the attending physician based upon clinical factors unique to each patient. The optimal daily dose will be determined by methods known in the art and will be influenced by factors such as the age of the patient as indicated above and other clinically relevant factors. In addition, patients may be taking medications for other diseases or conditions. The other medications may be continued during the time that the agent is given to the patient, but it is particularly advisable in such cases to begin with low doses to determine if adverse side effects are experienced.

Carriers/vehicles

The compound or agent of the present invention (e.g., 4-P-PDOT, a derivative, analog, conjugate or prodrug of 4-P-PDOT; or a pharmaceutical acceptable salt thereof) may be incorporated into dosage forms in conjunction with any of the vehicles which are commonly employed in pharmaceutical preparations, e.g., talc, gum arabic, lactose, starch, magnesium searate, cocoa butter, aqueous or non-aqueous solvents, oils, paraffin derivatives or glycols. Emulsions such as those described in U.S. Pat. No. 5,434,183 may also be used in which vegetable oil (e.g., soybean oil or safflower oil), emulsifying agent (e.g., egg yolk phospholipid) and water are combined with glycerol. Further non-limiting pharmaceutically suitable materials that may be incorporated in pharmaceutical preparations of the present invention include absorption enhancers, pH regulators and buffers, osmolarity adjusters, preservatives, stabilizers, antioxidants, surfactants, thickeners, emollient, dispersing agents, flavoring agents, coloring agents and wetting agents. Methods for preparing appropriate formulations are well known in the art (see e.g., Remington's Pharmaceutical Sciences, 16th Ed., 1980, A. Oslo Ed., Easton, Pa.).

In cases where parenteral administration is elected as the route of administration, preparations containing the agent may be provided to patients in combination with pharmaceutically acceptable sterile aqueous or non-aqueous solvents, suspensions or emulsions. Examples of non-aqueous solvents are propylene glycol, polyethylene glycol, vegetable oil, fish oil, and injectable organic esters. Aqueous carriers include water, water-alcohol solutions, emulsions or suspensions, including saline and buffered medical parenteral vehicles including sodium chloride solution, Ringer's dextrose solution, dextrose plus sodium chloride solution, Ringer's solution containing lactose, or fixed oils. Intravenous vehicles may include fluid and nutrient replenishers, electrolyte replenishers, such as those based upon Ringer's dextrose, and the like.

In yet another embodiment, the pharmaceutical compositions of the present invention can be delivered in a controlled release system. In embodiments, polymeric materials including polylactic acid, polyorthoesters, cross-linked amphipathic block copolymers and hydrogels, polyhydroxy butyric acid and polydihydropyrans can be used (see also Smolen and Ball, Controlled Drug Bioavailability, Drug product design and performance, 1984, John Wiley & Sons; Ranade and Hollinger, Drug Delivery Systems, pharmacology and toxicology series, 2003, $2^{nd}$ edition, CRRC Press), in another embodiment, a pump may be used (Saudek et al., 1989, N. Engl. J. Med. 321: 574). Compounds of the present invention may also be delivered by the use of targeting molecules and/or moiety (e.g., a monoclonal antibody, a peptide) as individual carriers to which the agent is coupled/associated. In an embodiment, the above-mentioned targeting molecule/moiety increases and/or facilitates the delivery of the agent to the bone (i.e. bone-targeting molecule/moiety). The present invention also encompasses compounds modified to increase their solubility and/or their circulatory time, such as their pegylation.

As used herein, "subject" or "subject in need thereof" refers to animals such as humans in which prevention, delay or treatment of a bone resorption defect is desirable. In particular embodiments, subjects having diseases or conditions such as osteoporosis, Paget disease and osteolytic bone cancer would benefit from the compounds, compositions, methods and uses of the present invention.

Other objects, advantages and features of the present invention will become more apparent upon reading of the following non-restrictive description of specific embodiments thereof, given by way of example only with reference to the accompanying drawings.

Figure 5:
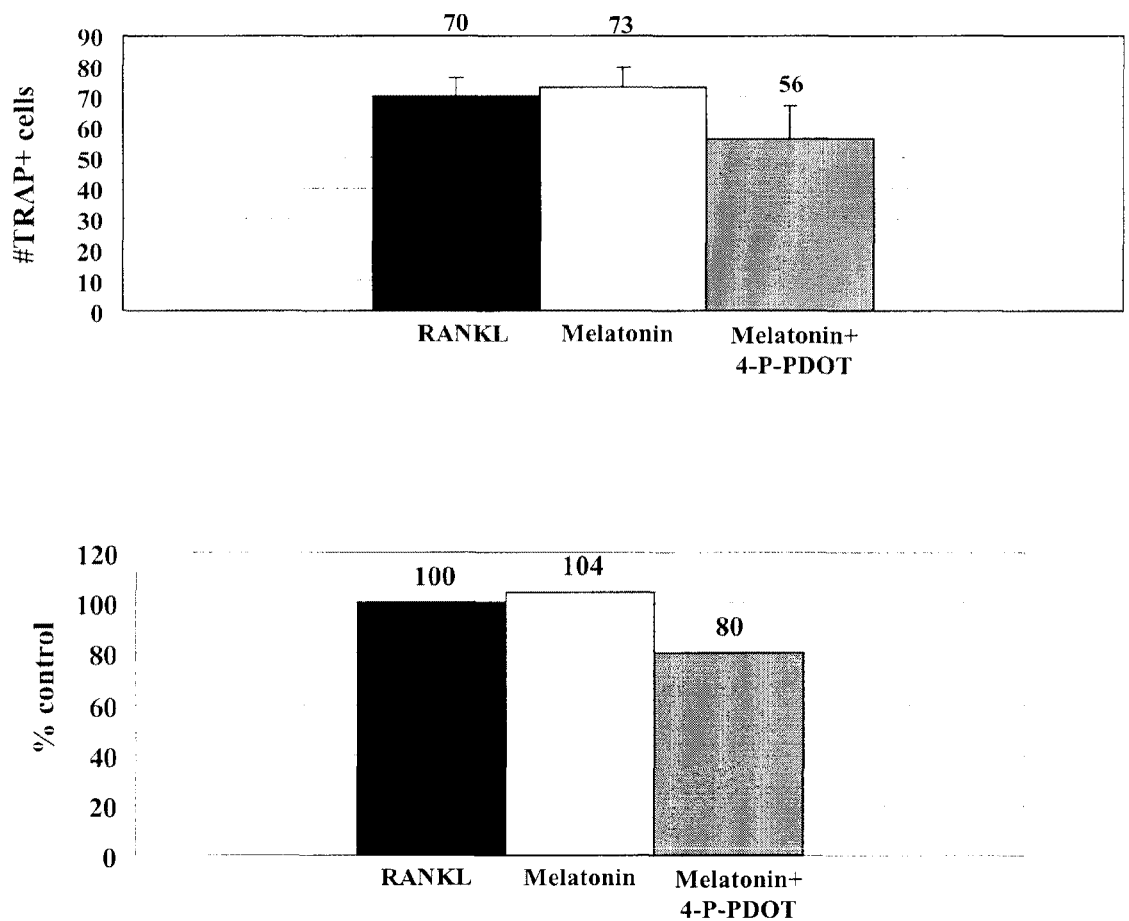
Figure 5:
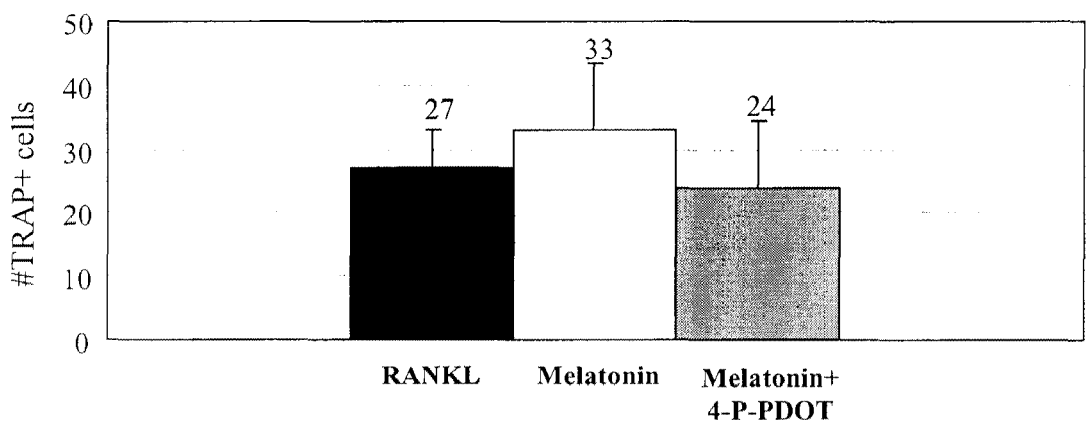
Figure 5:
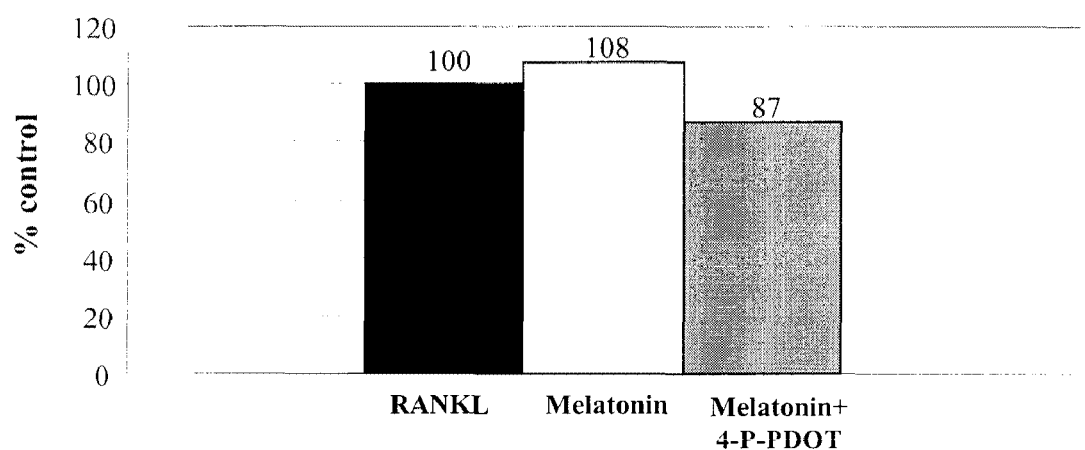
Figure 6:
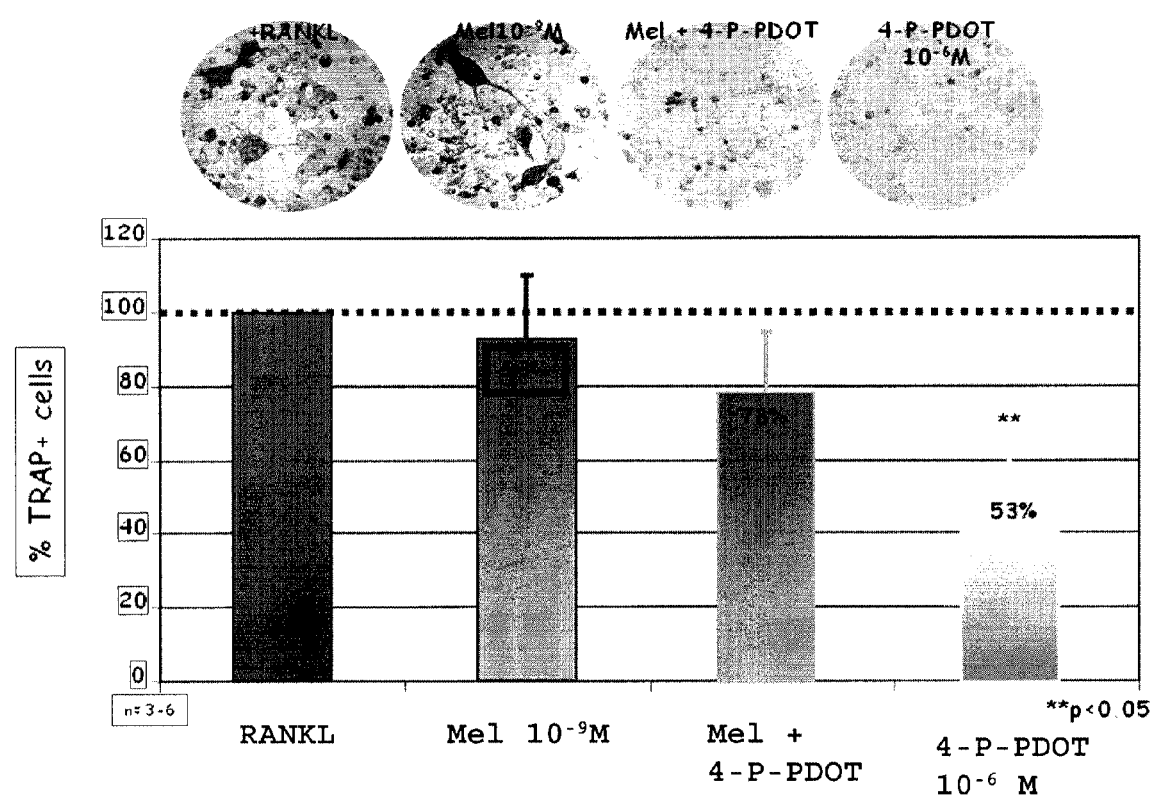
Figure 7:
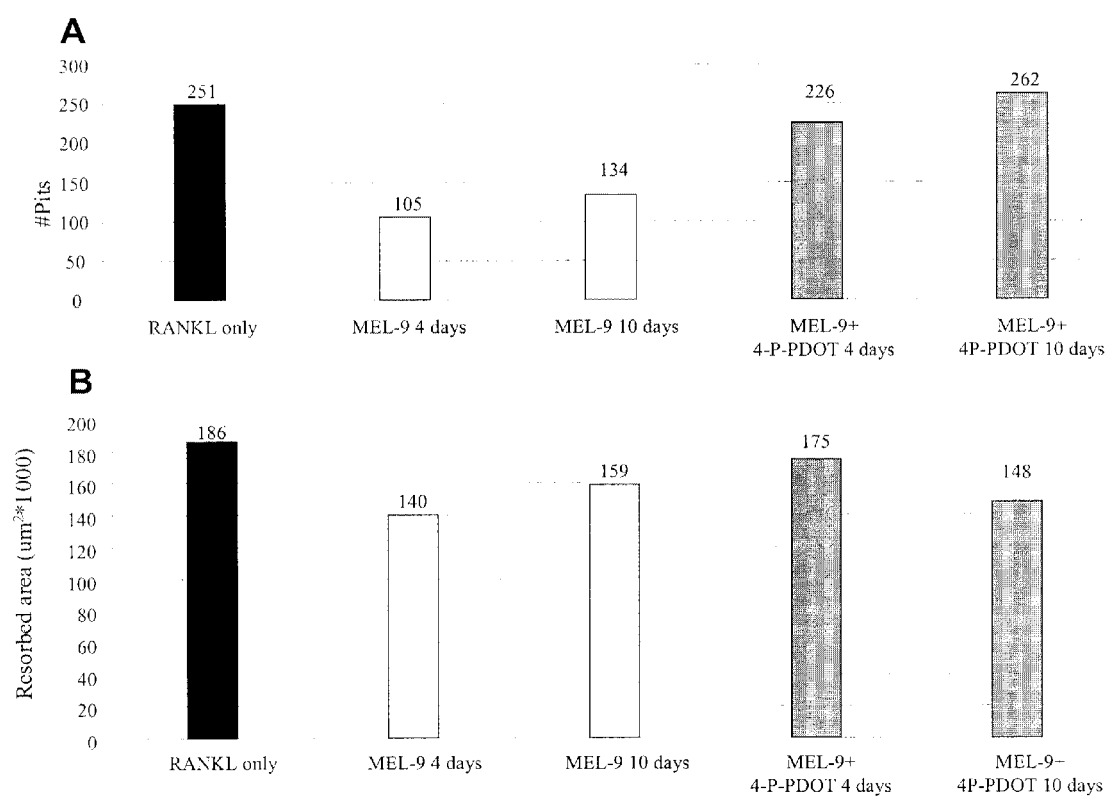
Figure 7:
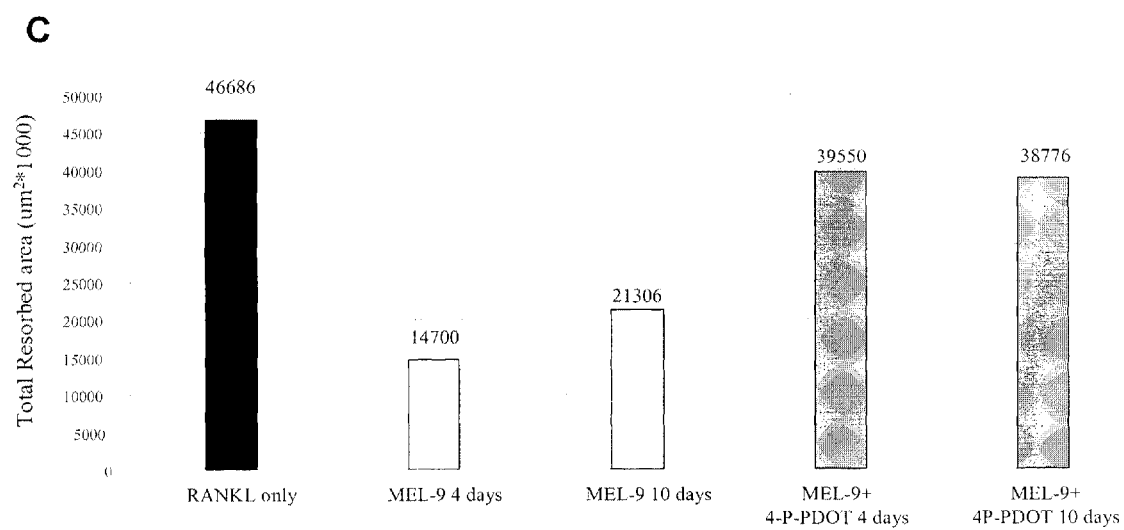
Figure 8:
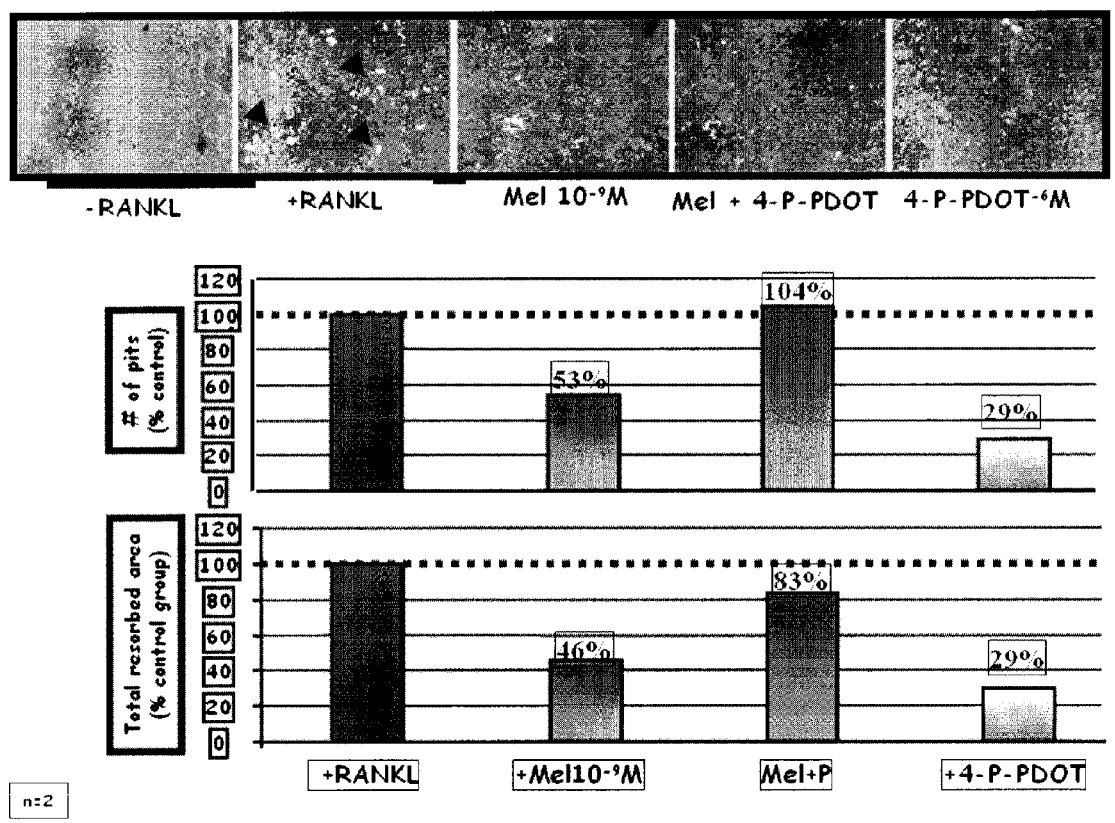
Figure 9:
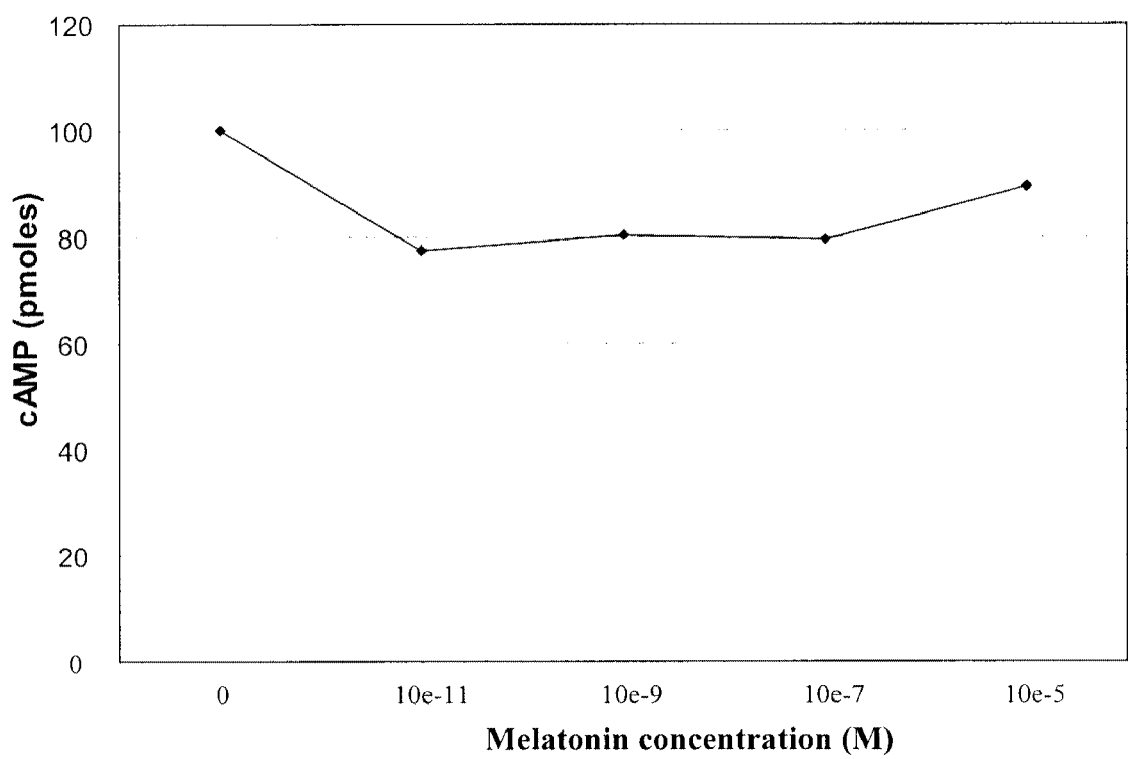
Figure 9:
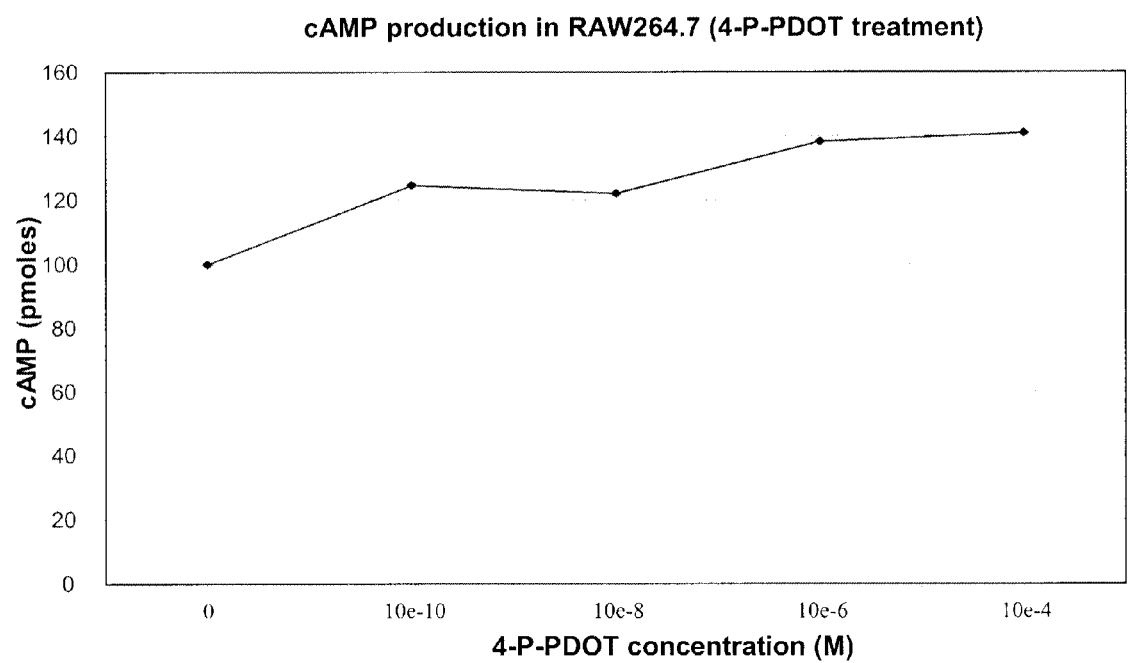
Figure 9:
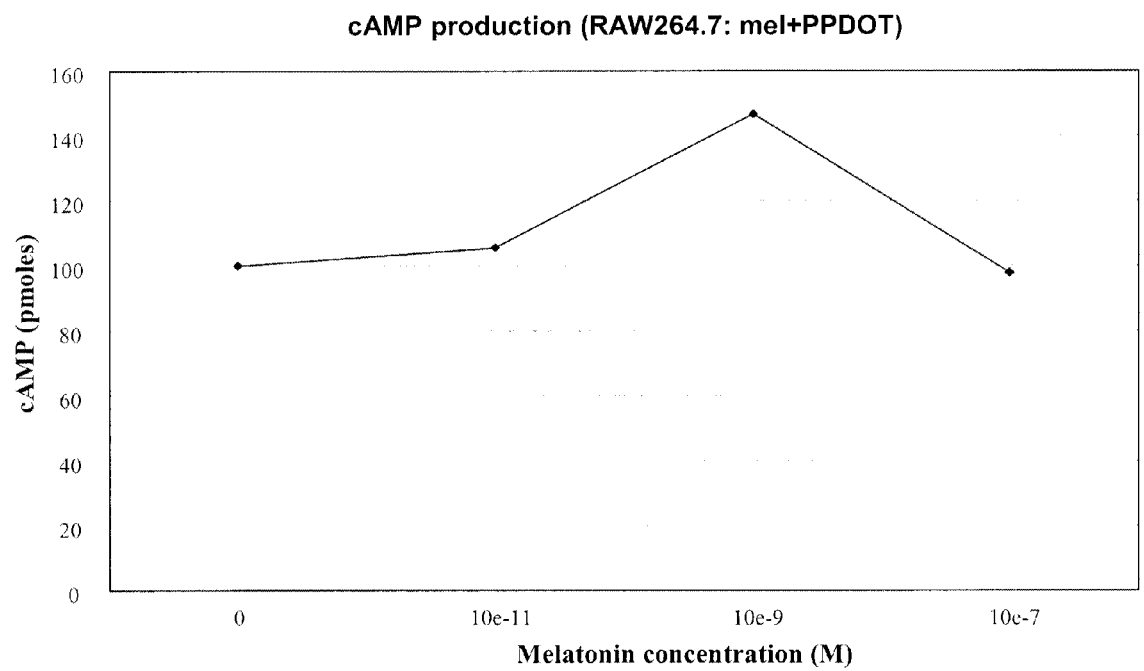
Figure 10:
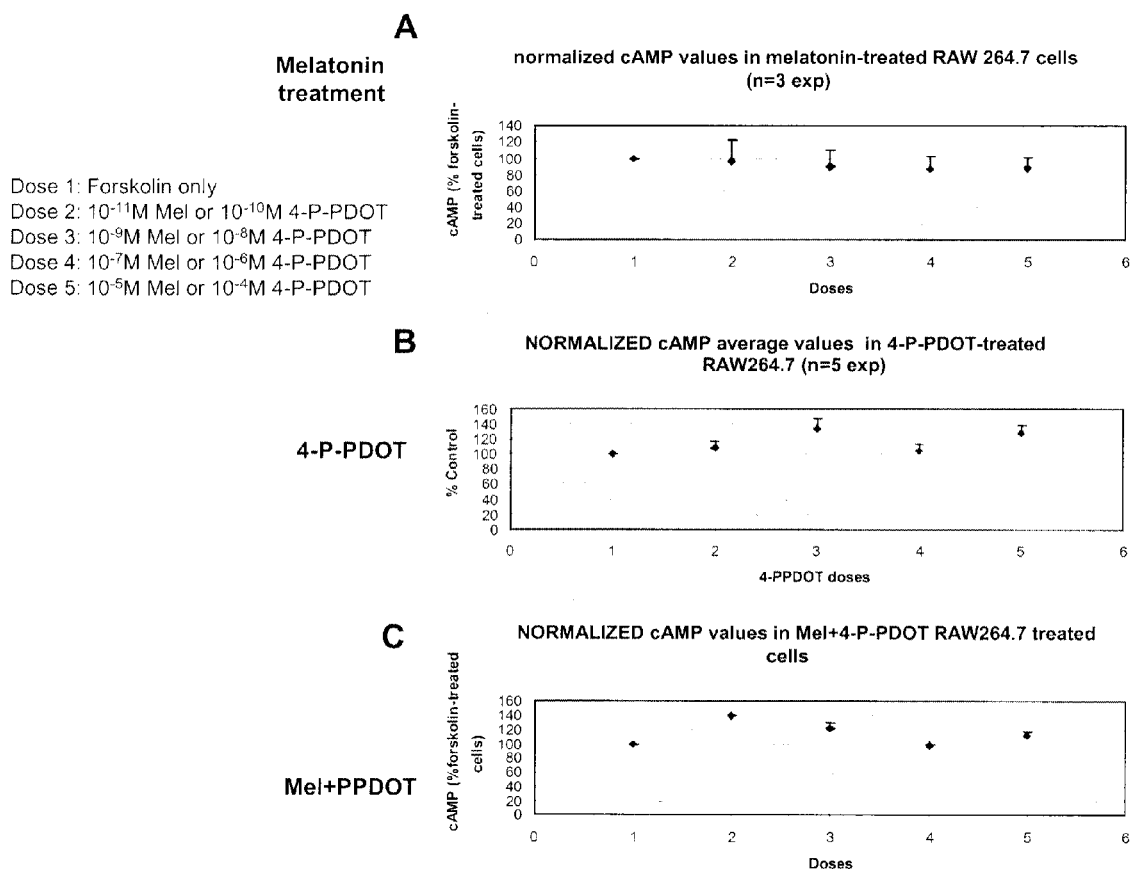
Figure 11:
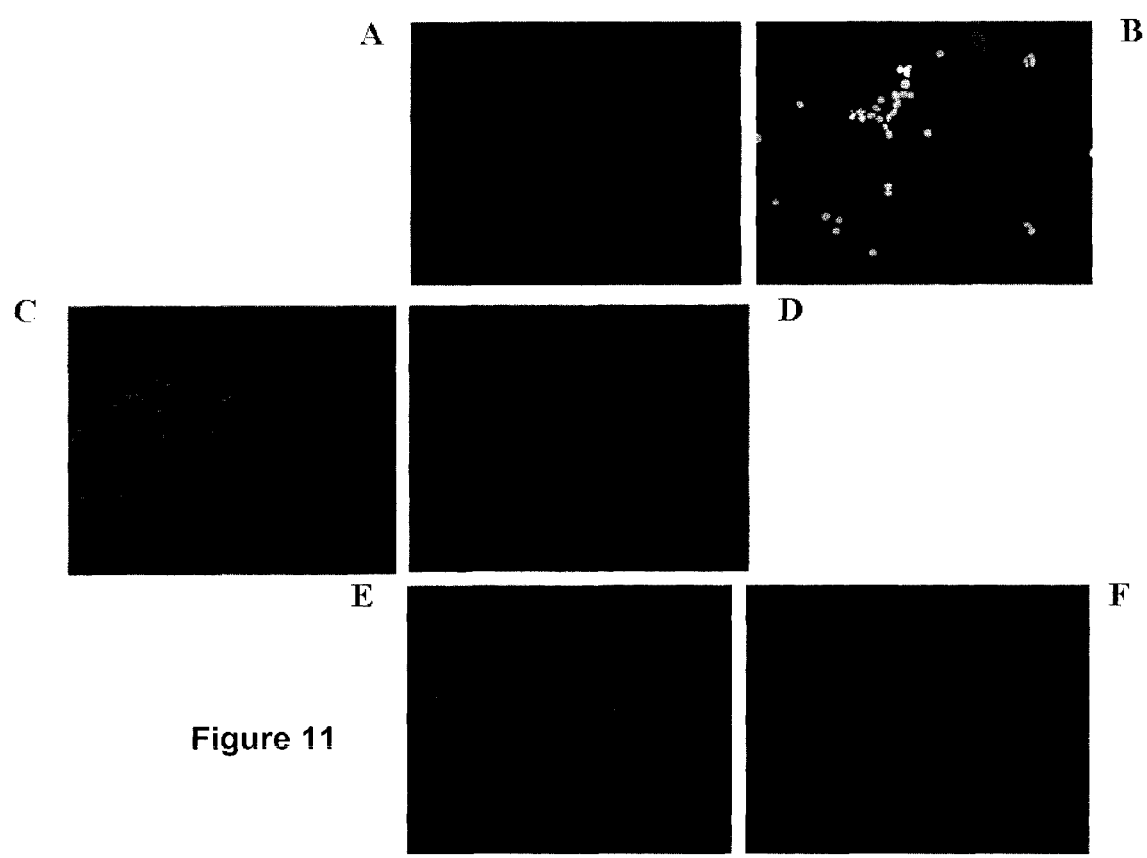
Figure 12:
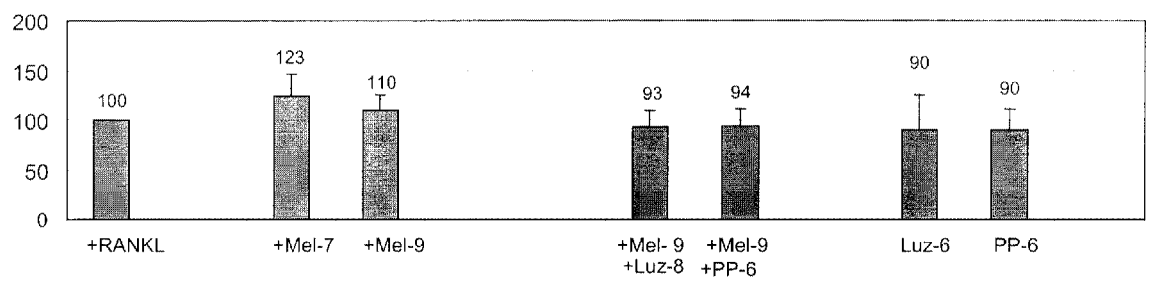
Figure 13:
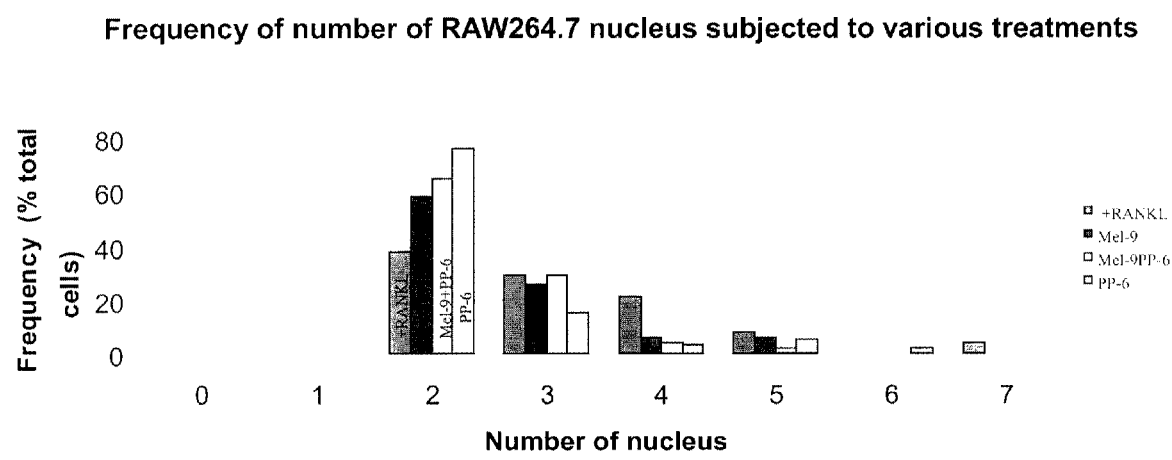
Figure 14:
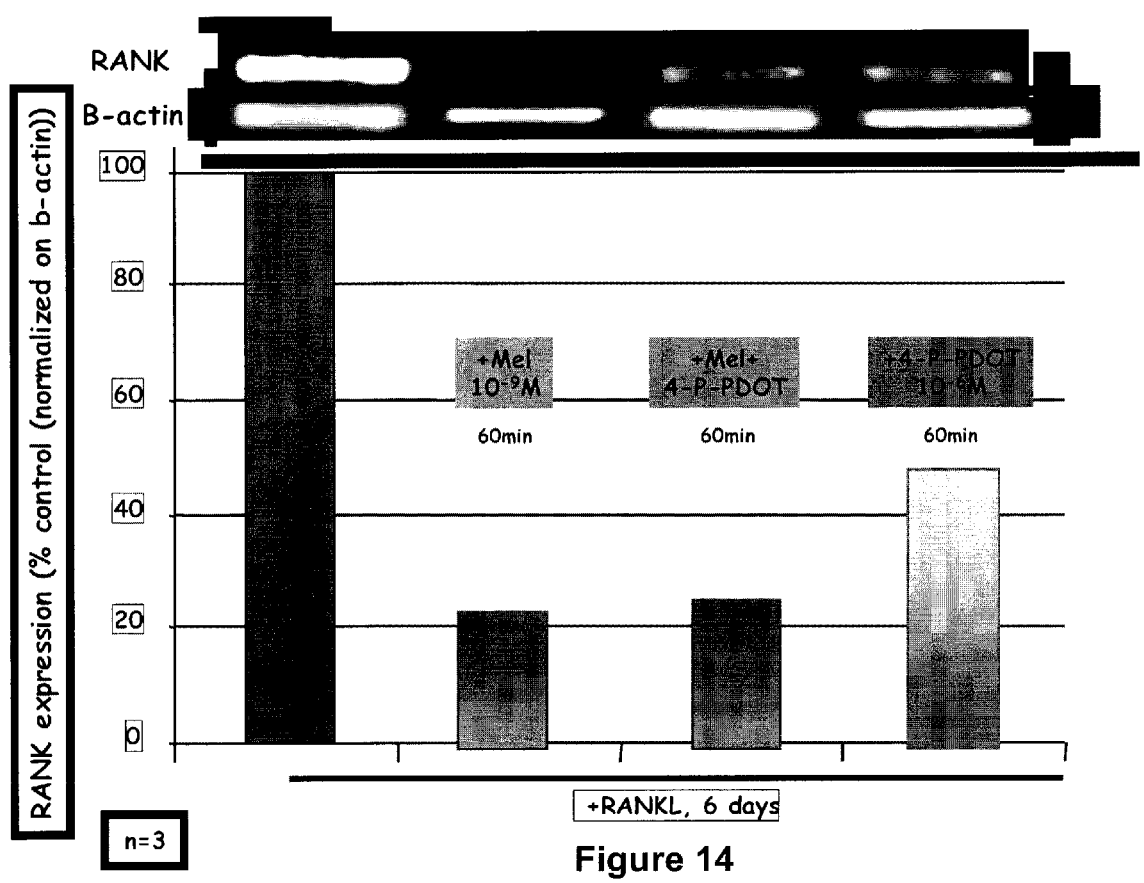
Figure 15:
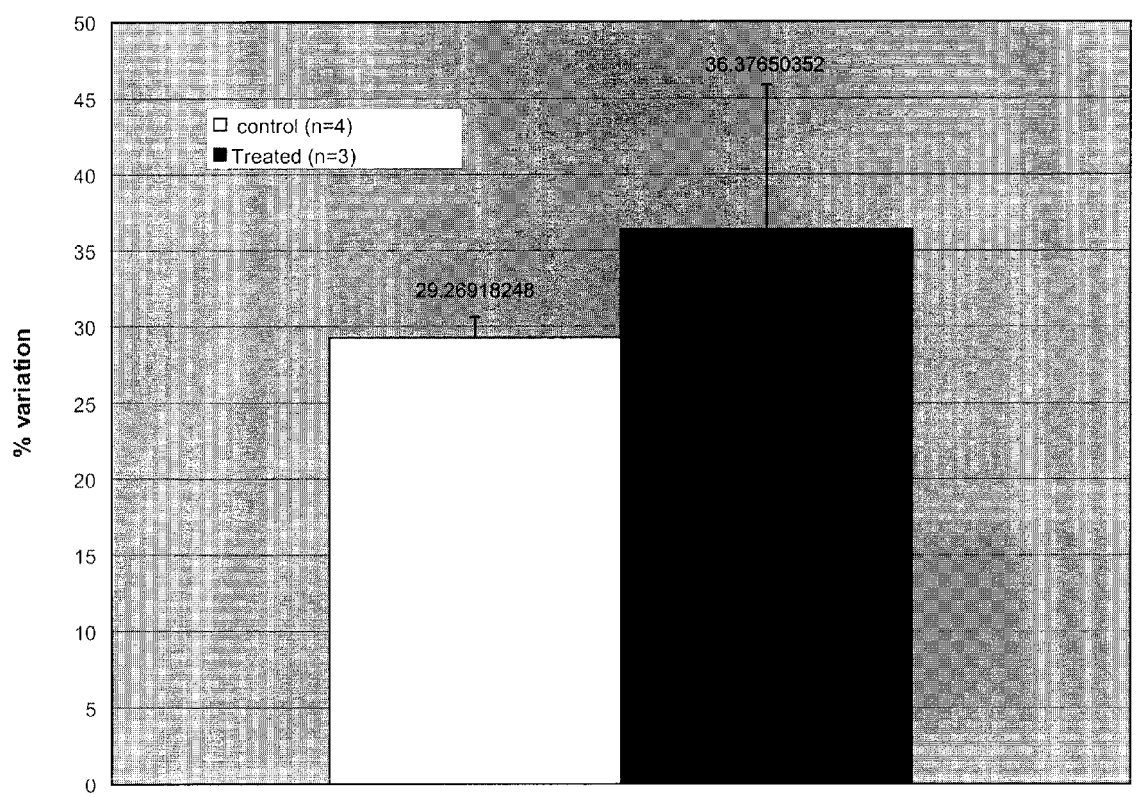
Figure 16:
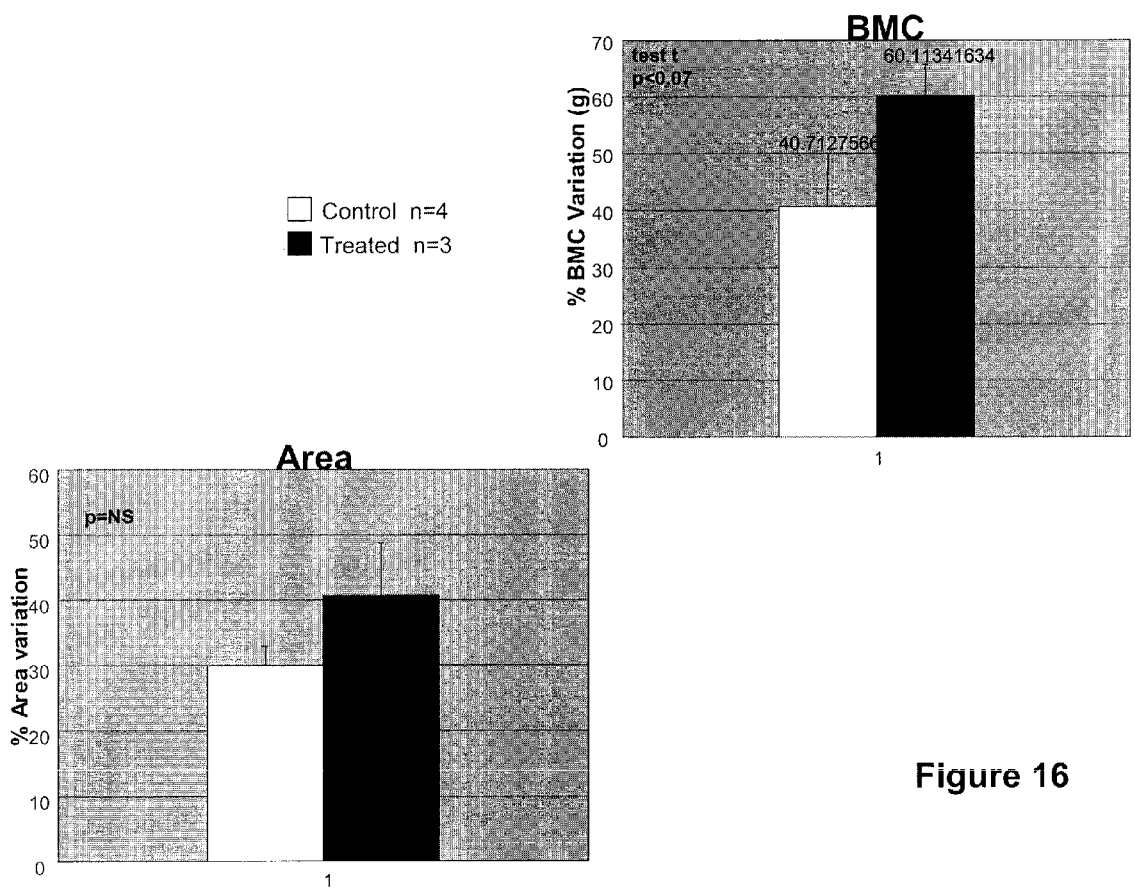
Figure 16:
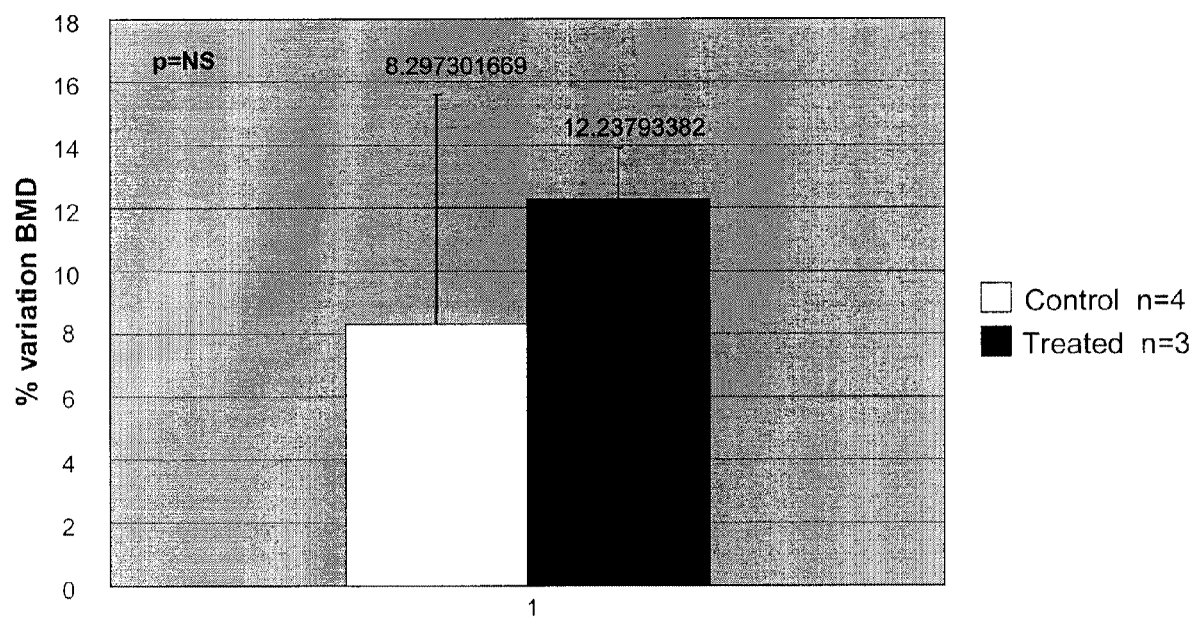
Figure 17:
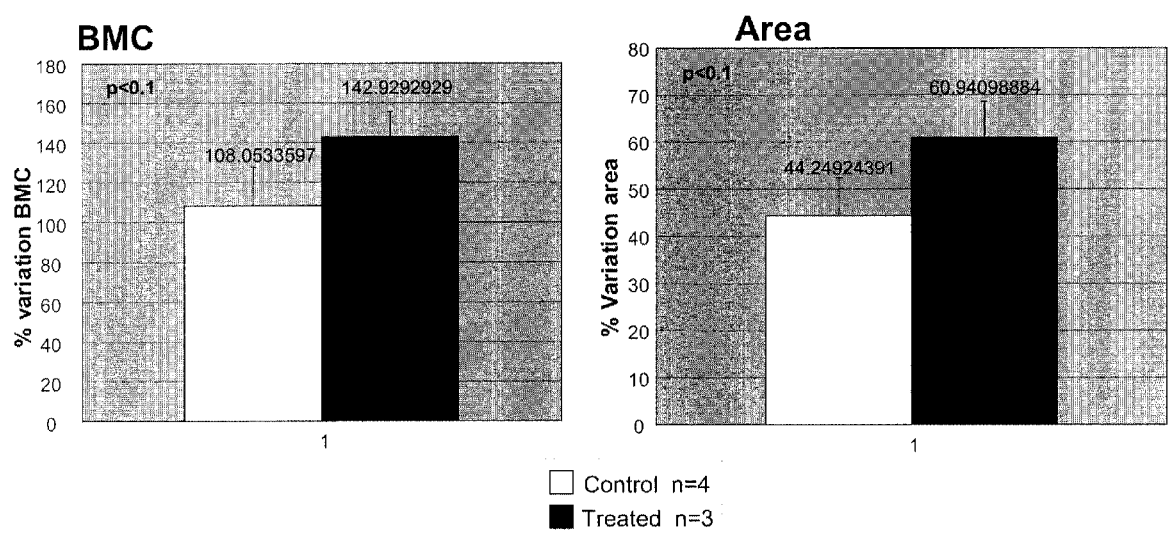
Figure 17:
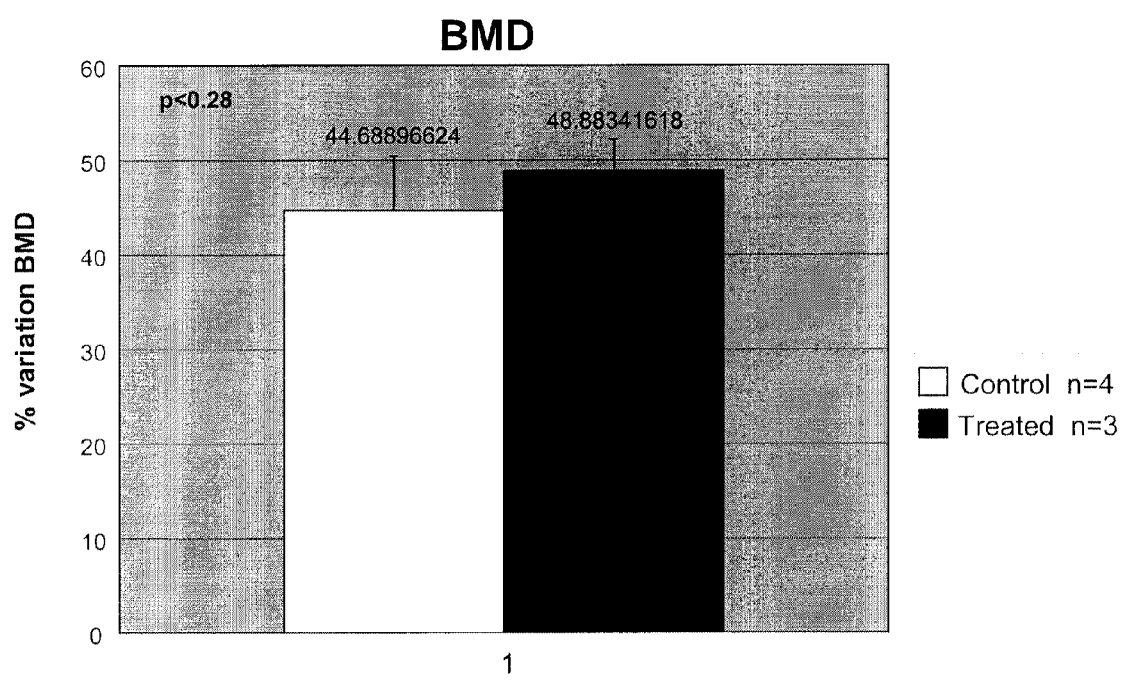
Figure 18:
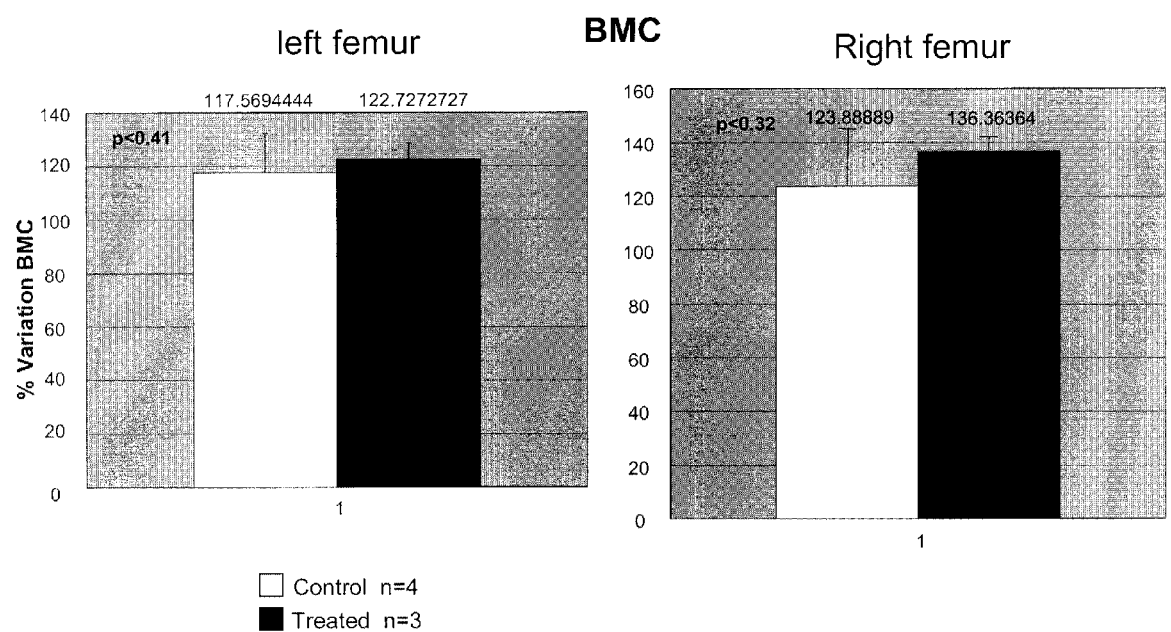
Figure 18:
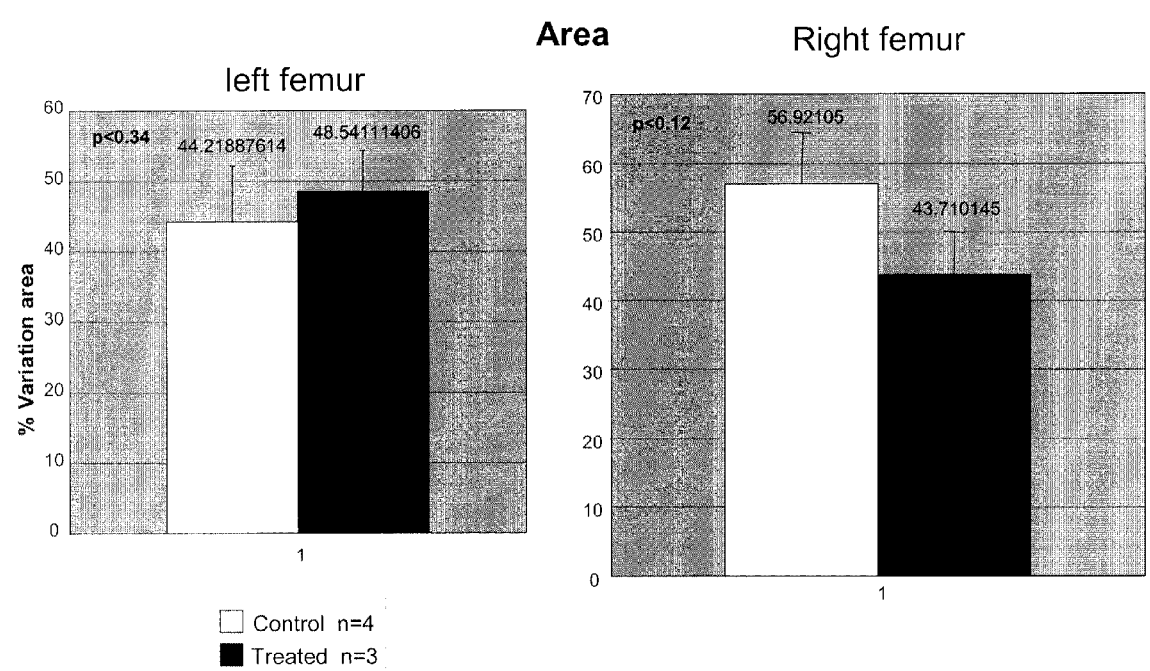
Figure 18:
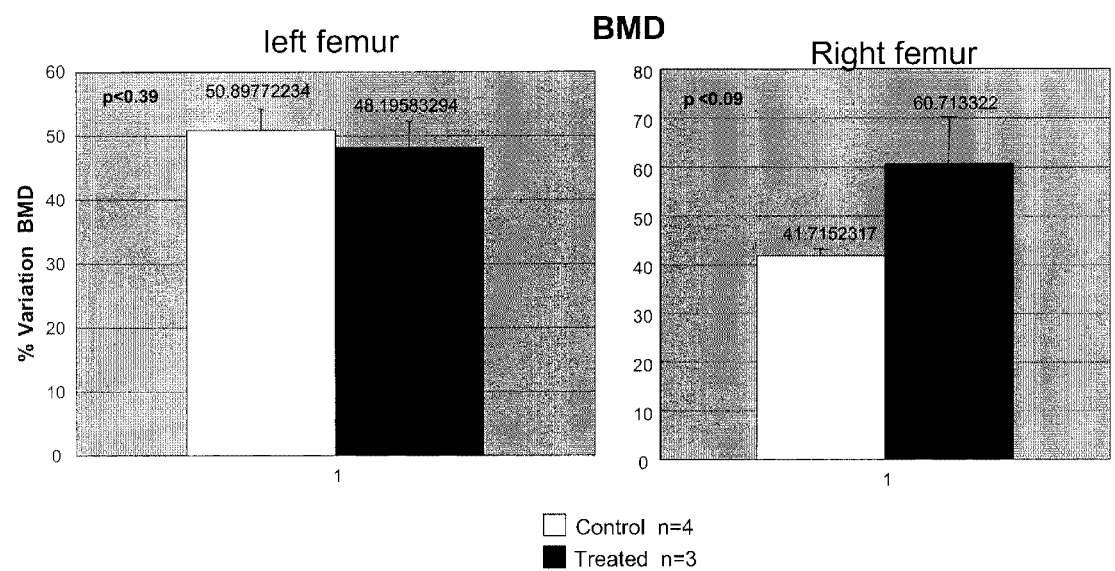
Figure 19:
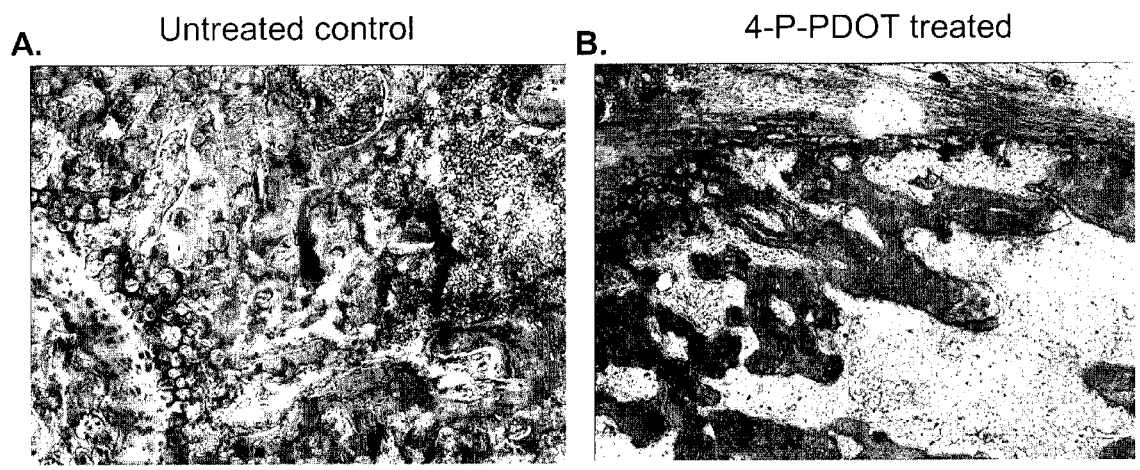
Figure 20:
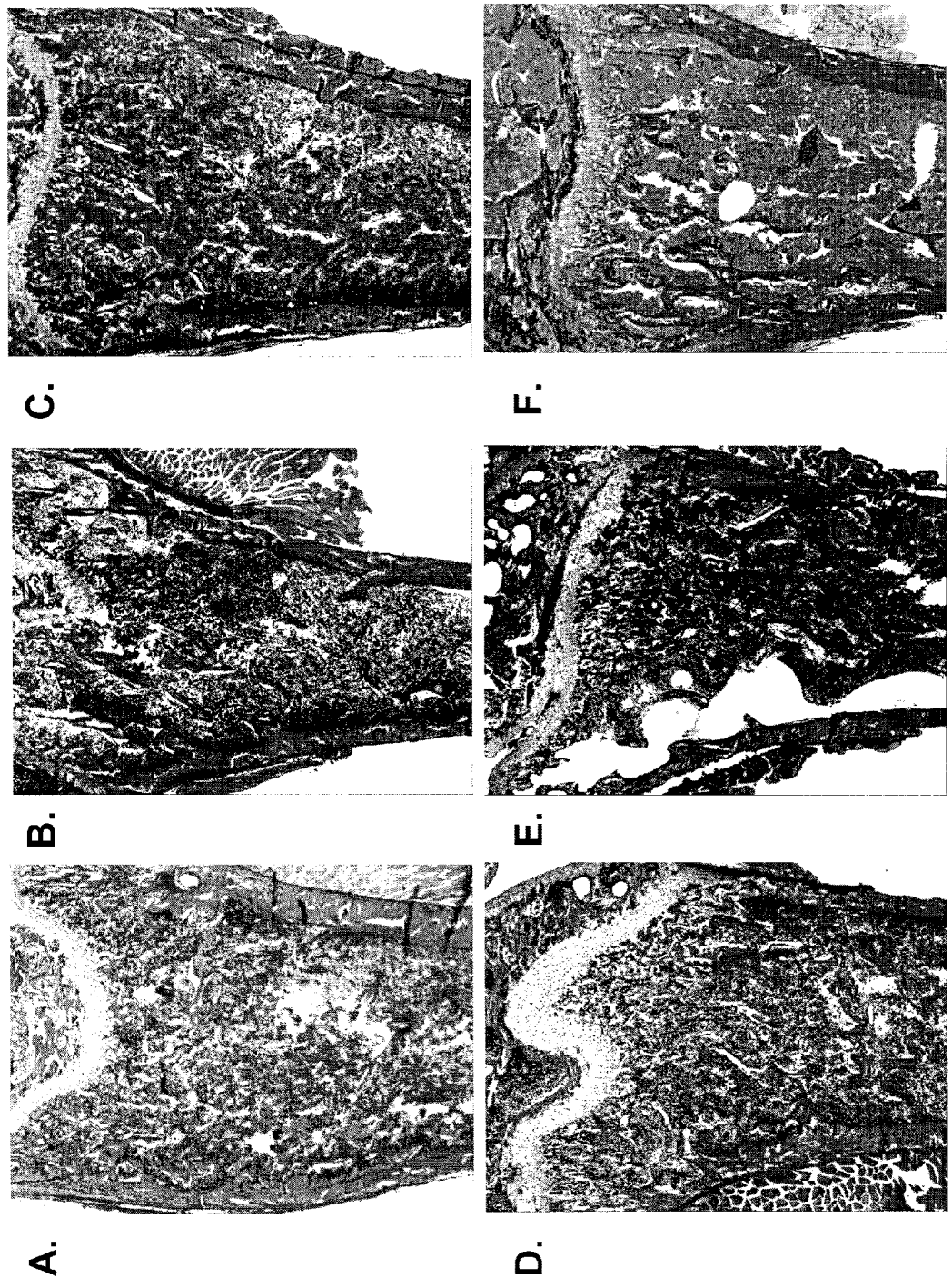

(hatched bars) days. Results of eight microscopic fields counted in duplicate are illustrated. Results summarize 2 independent experiments;

FIG. 5 presents the effect of melatonin on osteoclasts differentiation. RAW264.7 cells were cultured with RANKL for 2.5 (panel A) or 6 (panel B) days without (black bars), with $10^{-9}$M of melatonin (white bars) and with melatonin $+10^{-6}$M 4-P-PDOT (grey bars). Raw counts (upper panel) and % of control cells (lower panel) are indicated. These results represent the average of 4 independent experiments;

FIG. 6 compares the differentiation of RAW264.7 cells cultured with RANKL for 6 days with $10^{-9}$M of melatonin, $10^{-9}$M melatonin $+10^{-6}$M 4-P-PDOT, or $10^{-6}$M 4-P-PDOT in terms of percentage of TRAP-positive cells over control (cells treated with RANKL only). The upper panel presents microscopic fields showing cells after each treatment. These results represent the average of 3 to 6 independent experiments;

FIG. 7 presents the effect of melatonin on osteoclasts function. RAW264.7 cells were cultured with RANKL for 10 days without (black bars), with $10^{-9}$M of melatonin (white bars), or with $10^{-9}$M of melatonin $+10^{-6}$M of 4-P-PDOT (grey bars) for 4 or 10 days. Number of resorption pits (panel A), resorbed area ($\mu m^2 *1000$) (panel B) and total resorbed area (number of pits X resorbed area ($\mu m^2 *1000$)) (panel C) of eight microscopic fields counted in duplicate are illustrated. These results summarize 2 independent experiments;

FIG. 8 compares the differentiation of RAW264.7 cells cultured with RANKL for 10 days with $10^{-9}$M of melatonin, $10^{-9}$M melatonin $+10^{-6}$M 4-P-PDOT, or $10^{-6}$M 4-P-PDOT in terms of percentage of number of resorption pits (middle panel) or total resorbed area (lower panel) over control (cells treated with RANKL only). The upper panel presents microscopic fields showing cells after each treatment. These results summarize 2 independent experiments;

FIG. 9 shows the effect of increasing concentrations of melatonin (panel A), 4-P-PDOT (panel B) or both (panel C) on adenylyl cyclase activity of forskolin-stimulated RAW 264.7 cells;

FIG. 10 shows the normalized cAMP values of forskolin-stimulated RAW 264.7 cells resulting from increasing concentrations of melatonin (upper panel, A), 4-P-PDOT (middle panel, B) or both (lower panel, C);

FIG. 11 shows a comparison of cell apoptosis in differentiated RAW 264.7. Negative control without primary antibody (panel A). DNase-treated cells as positive controls for apoptosis (panel B). Cells treated with RANKL only (panel C), 4-P-PDOT $10^{-6}$M (panel D), Melatonin $10^{-9}$M (panel E) and Melatonin $10^{-9}$M+4-P-PDOT $10^{-6}$M (panel F);

FIG. 12 presents tritiated-thymidine incorporation in RAW264.7 cells treated with RANKL only, $10^{-7}$M (+mel-7) or $10^{-9}$M (+mel-9) melatonin, $10^{-6}$M luzindole (Luz-6), $10^{-6}$M 4-P-PDOT (PP-6), $10^{-9}$M melatonin+$10^{-8}$M luzindole (+mel-9+Luz-8) or $10^{-9}$M melatonin+$10^{-6}$M 4-P-PDOT (+mel-9+PP-6);

FIG. 13 presents the frequency of the number of RAW264.7 nuclei subjected to RANKL only, $10^{-9}$M melatonin (mel-9), $10^{-6}$M 4-P-PDOT (PP-6), or $10^{-9}$M melatonin+$10^{-6}$M 4-P-PDOT (+mel-9+PP-6);

FIG. 14 presents RANK cDNA expression on RAW264.7 cells cultured with RANKL for 10 days with $10^{-9}$M of melatonin, $10^{-9}$M melatonin+$10^{-6}$M 4-P-PDOT, or $10^{-6}$M 4-P-PDOT in terms of percentage of expression (normalized over β-actin expression) over control (lower panel). The upper panel presents RANK cDNA expression (following RT-PCR) on an agarose gel in cells following the different treatments. These results summarize 3 independent experiments;

FIG. 15 presents the weight gain variations from day 0 to day 35 in control and treated mice;

FIG. 16 presents bone mineral content (BMC), bone area, and bone mineral density (BMD) variations from day 0 to day 35 in whole body of control and treated mice;

FIG. 17 presents BMC, bone area, and BMD variations from day 0 to day 35 in spine of control and treated mice;

FIG. 18 presents BMC, bone area, and BMD variations from day 0 to day 35 in left and right femurs of control and treated mice;

FIG. 19 presents TRAP staining on right femur section of male C57Bl6/j mice. Panel A represents a right femur section of a control mouse (untreated). Panel B represents a right femur section of a mouse treated with 4-P-PDOT at 10 mg/kg of body weight. There is a significant reduction in the number of osteoclasts in mice treated with 4-P-PDOT. Magnification 20×;

FIG. 20 presents Goldner staining of right femur sections of male C57Bl/6j mice. Upper panels (A, B and C) represent histological sections of untreated mice (n=3, controls), while lower panels (D, E and F) represent histological sections of mice treated with 4-P-PDOT (n=3). Trabecular bone is increased in animal treated with 4-P-PDOT (10 mg/kg of body weight IP injection three times per week); and FIG. 21 shows the effect of 4-P-PDOT on the number of total osteoclasts vs. active osteoclasts. Total osteoclast numbers were determined on Goldner stained sections while active osteoclasts were calculated based on the number of TRAP$^+$ cells.

DESCRIPTION OF ILLUSTRATIVE EMBODIMENTS

The present invention is illustrated in further detail by the following non-limiting examples.

Cellular model RAW264.7 (mouse macrophage cell line, ATCC #TIB-71). These cells differentiate in osteoclast-like cells upon addition of receptor activator of nuclear factor-kappaB ligand (RANKL). Cell differentiation usually occurs within two days. Cells were studied at 2.5 (early stage), 6 and 10 days (late stage) following RANKL addition.

Experimental treatments: In some experiments, 4-P-PDOT was added to the cells at the same time as RANKL at a concentration of $10^{-6}$M. Cells cultured with RANKL only served as controls.

EXAMPLE 1

Gene and Protein Expression of Melatonin Receptors on RAW264.7 Cells

Figure 1:
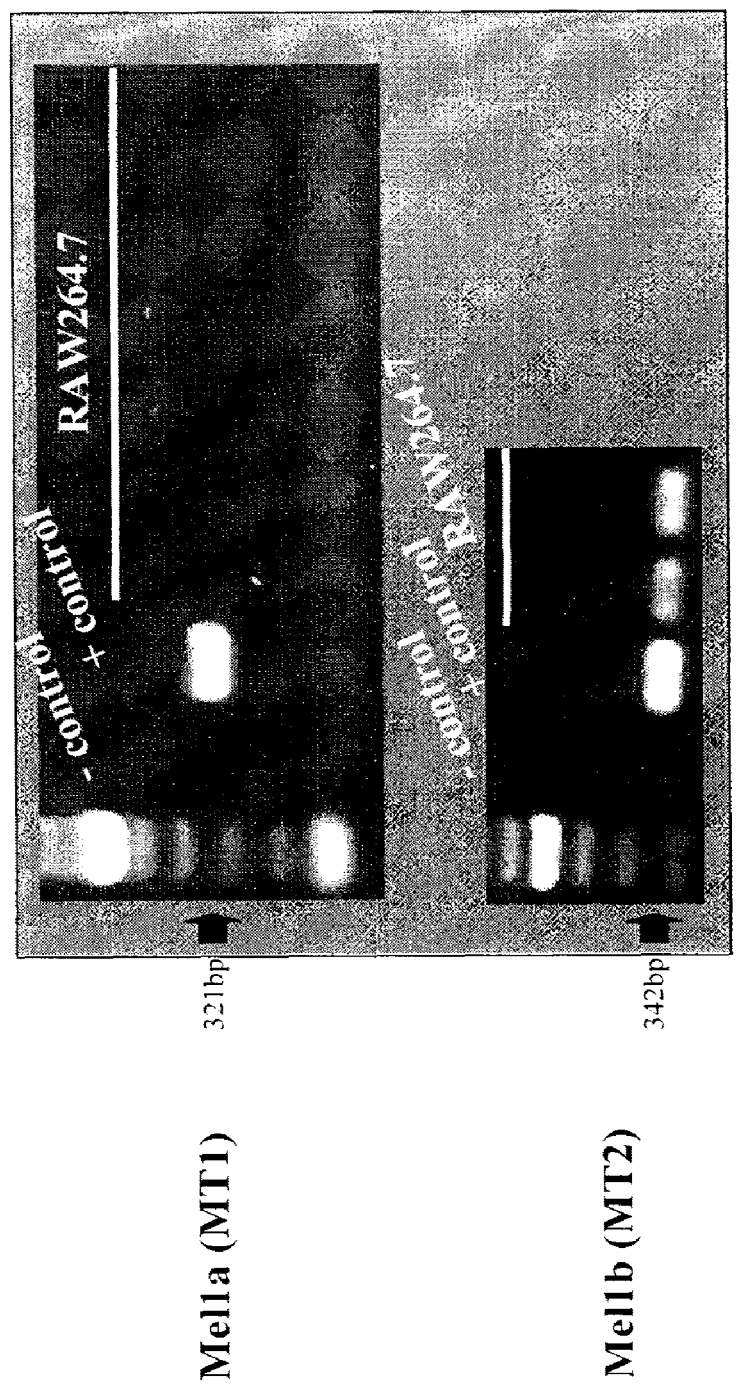
FIG. 1 presents RT-PCR results showing that only Mel1b (MT2) is expressed in RAW264.7 cells. Brain tissue served as positive controls (+control)

In order to determine the presence of melatonin receptors on RAW 264.7 cells, gene and protein expression was examined. RAW264.7 cells were cultured with or without RANKL for a period of 6 days. RNA was extracted using Trizol™ reagent according to the manufacturer's instructions. 2 µg of total RNA were reverse transcribed using Thermoscript™ RT-PCR system (InVitrogen). PCR reactions for melatonin receptors 1a (MT1) and 1b (MT2) were set up using intron spanning primers. MT2 Forward: 5'-GCAGG-TAATTTGTTTGTGGT-3' (SEQ ID NO: 1); MT2 Reverse: 5'-AGATGCGTGGATCATACTCT-3' (SEQ ID NO: 2); MT1 Forward: 5'-TGTACCGCAACAAGAAGCTCAGGA-3' (SEQ ID NO: 3); MT1 Reverse: 5'-TGGCGATGAGTGT-CAGCATCCATA-3' (SEQ ID NO: 4). RAW264.7 samples were compared to a brain tissue sample that was positive for both receptors. The results are presented in FIG. 1. MT2 was thus detected while MT1 was not.

Figure 2:
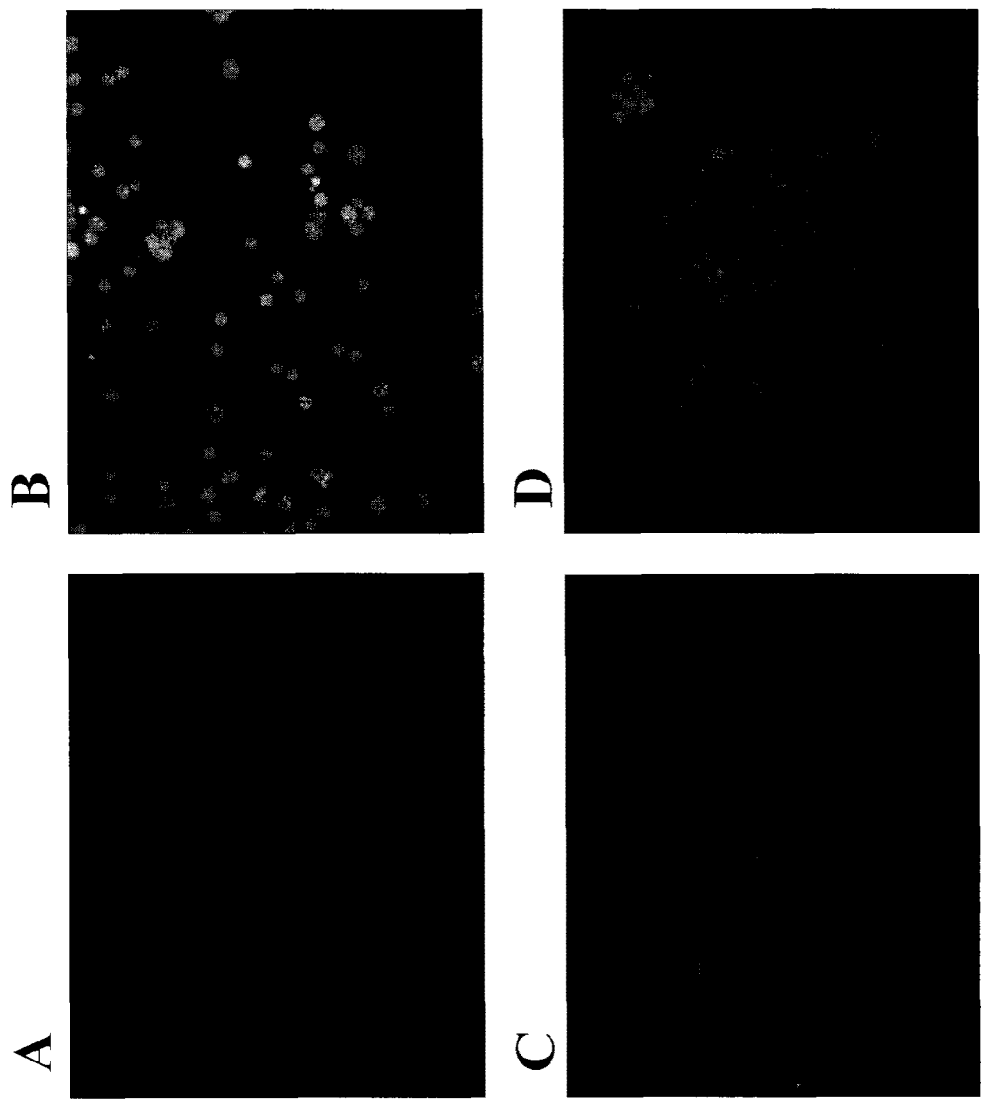
FIG. 2 presents differentiated RAW264.7 cells positively stained for MT2 receptor. Panel A: Negative control without primary antibody. Panel C: Cells stained with MT2 antibody illustrating the membrane localization of the protein. Panels B and D: DAPI nuclear stain of both negative control and MT2 positive cells. Panels E and F: Negative control (incubation in the presence of a peptide recognized by the antibody and competing with the MT2 receptor) and DAPI nuclear stain of this negative control, respectively.
Figure 2:
Figure 2:
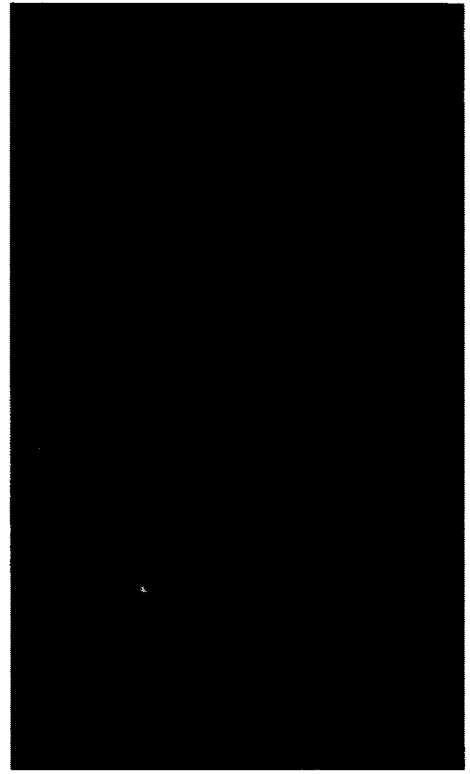

MT2 receptor localization was then investigated by immunofluorescence. RAW 264.7 cells were grown for three days with or without RANKL in LabTek™ chamber. Cells were fixed in 3.7% of paraformaldehyde and permeabilized with 0.1% Triton™-X-100. Cells were then incubated in PBS added with 1% bovine albumin (PBSA) for 30 minutes before a two-hour incubation with 1:25 dilution of anti-melatonin Ib in PBSA at 37° C. Negative controls were incubated with PBSA alone. After four rinses in PBS, cells were incubated one hour with 1:500 dilution of donkey anti-goat conjugated to Alexa™ 594 fluorochrome at 37° C. Cells were mounted and images visualized with 40× objective using a microscope equipped with fluorescence. Exposure times for each color were the same for all conditions. The results are presented in FIG. 2.

EXAMPLE 2

Figure 3:
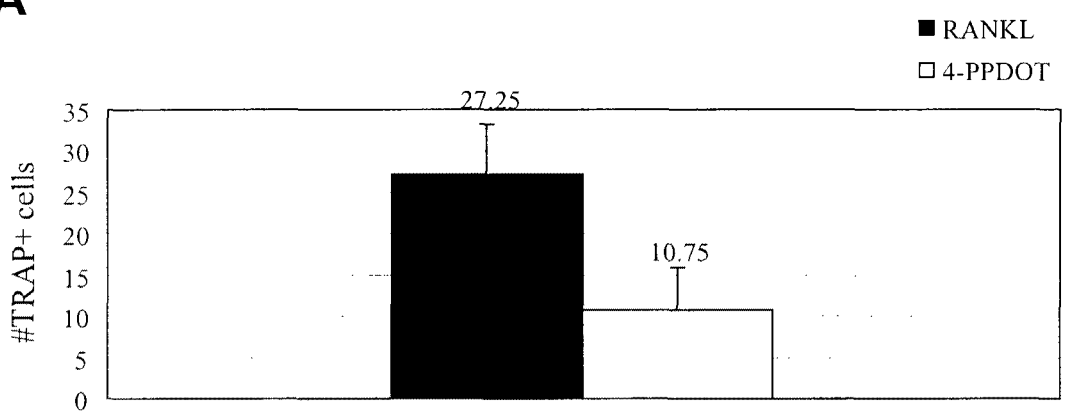
FIG. 3 presents the number of TRAP-positive RAW264.7 cells. The cells were cultured with RANKL for 2.5 (panel A) or 6 (panel B) days with (white bars) and without (black bars) $10^{-6}$M of 4-P-PDOT. Raw counts (upper panel) and % of control cells (lower panel) are indicated. These results represent the average of 3 independent experiments.
Figure 3:
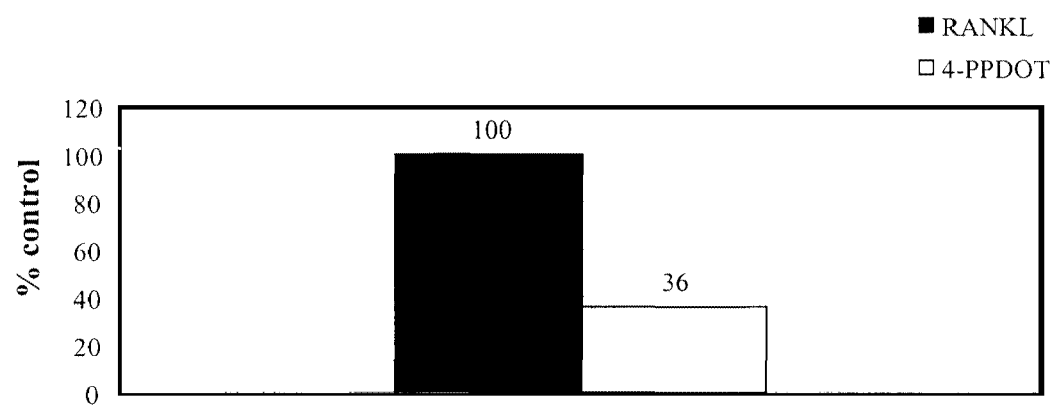
Figure 3:
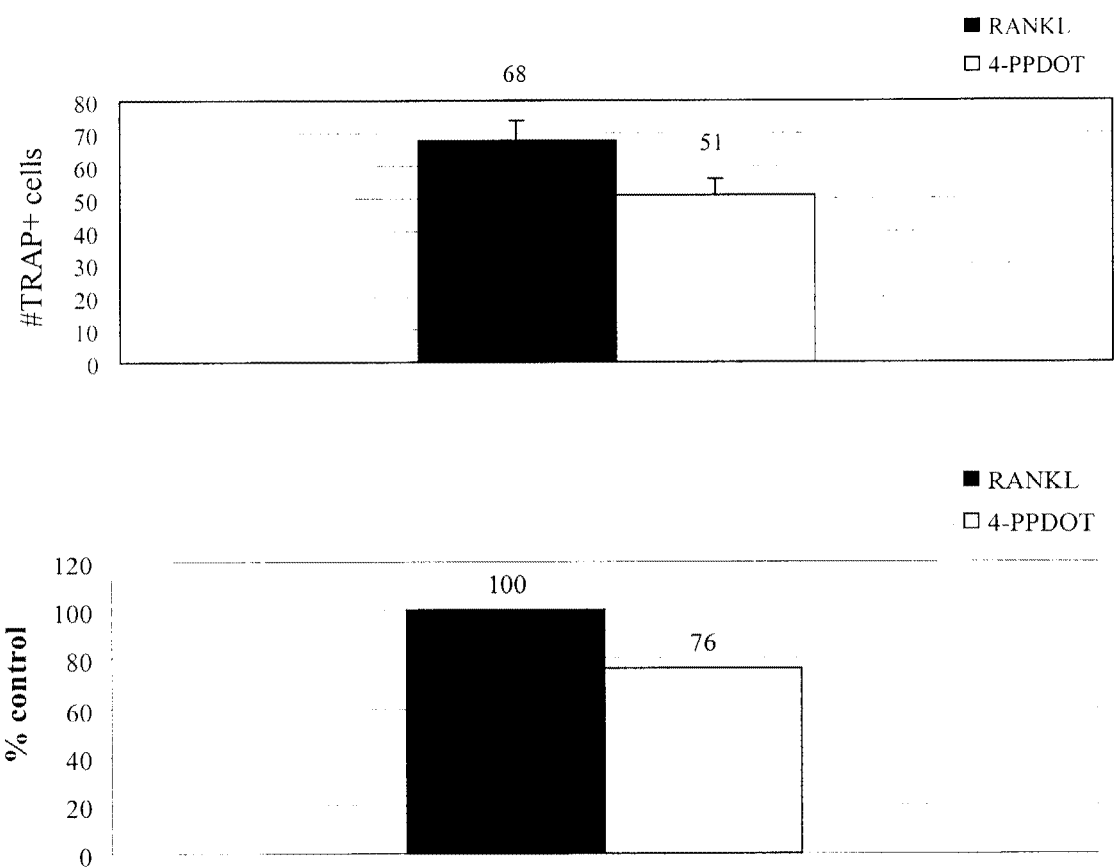

Effect of 4-P-PDOT on Osteoclast Differentiation as Measured by Tartrate Resistant Acid Phosphatase (TRAP) Activity In order to assess osteoclastogenesis, RAW264.7 cells were cultured with RANKL for 2.5 or 6 days with and without $10^{-6}$M of 4-P-PDOT. RAW264.7 cells were fixed with paraformaldehyde and stained for TRAP activity (marker of active osteoclasts) at 2.5 and 6 days of differentiation. Positive-stained cells with more than 3 nuclei were counted in eight different microscopic fields done in quadruplicate. Results are presented in FIGS. 3A and B for the 2.5 or 6 days experiments, respectively. The data show that addition of 4-P-PDOT during RAW264.7 cell differentiation reduces the number of TRAP+ cells.

EXAMPLE 3

Osteoclast Function: Bone Resorption Assay

Figure 4:
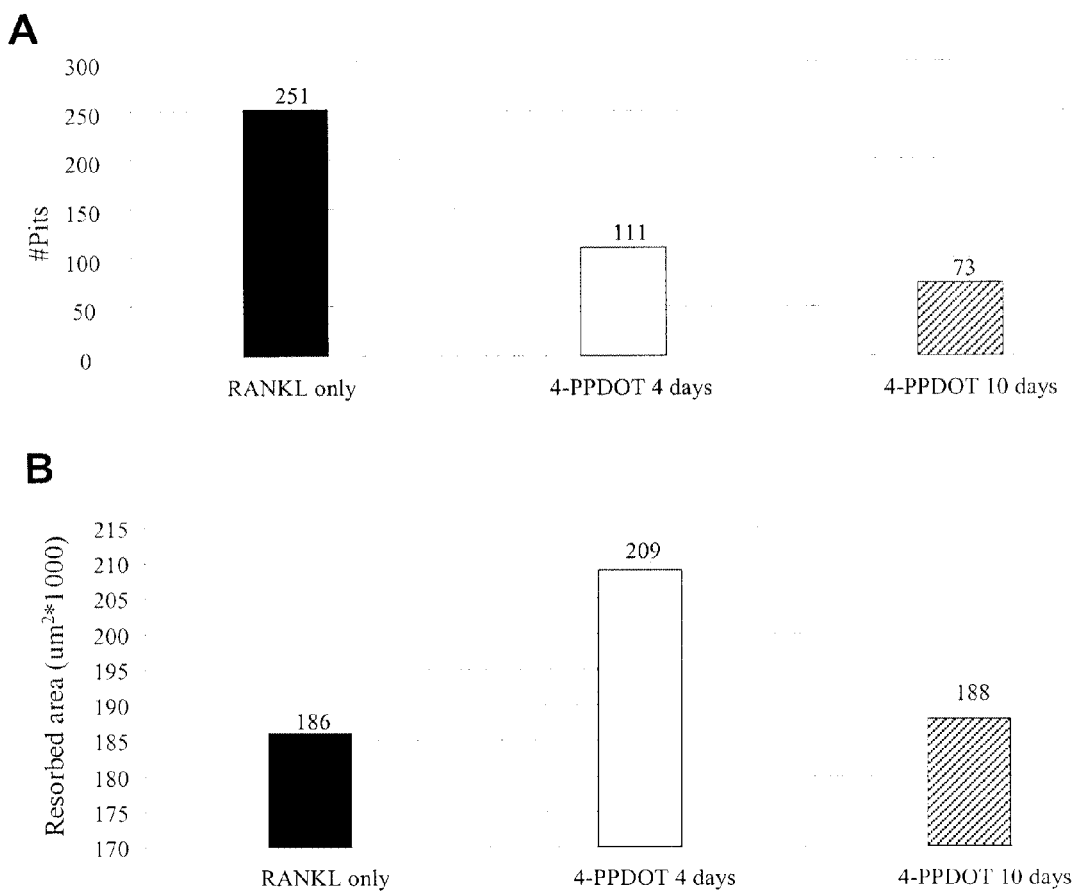
FIG. 4 presents bone resorption results. Panel A shows the number of resorption pits, panel B shows the resorbed area ($\mu m^2 * 1000$) and panel C shows the total resorbed area (number of pits X resorbed area ($\mu m^2 * 1000$)). RAW264.7 cells were cultured with RANKL for 10 days without (black bars), and with $10^{-6}$M of 4-P-PDOT for 4 (white bars) or 10
Figure 4:
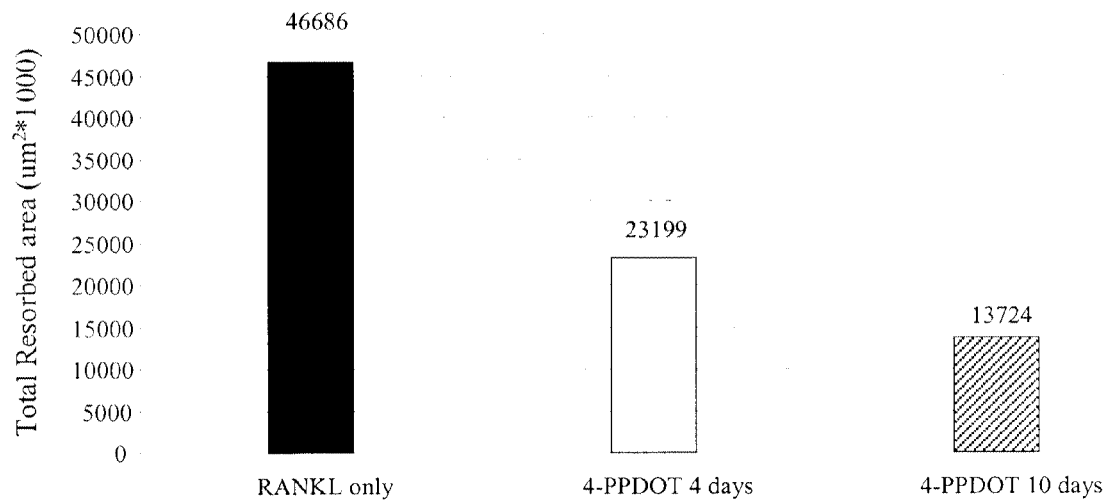

Osteoclast activity was determined using a resorbable bone analog (BioCoat™ Osteologic™ discs, BD Biosciences). RAW 264.7 cells were plated on 16-well plates coated with this analog. 24 hours post-plating, cells were treated with RANKL alone or with RANKL+$10^{-6}$M of 4-PPDOT for a period of 10 days. In another set of experiments, $10^{-6}$M of 4-P-PDOT was added after 6 days of culture with RANKL and cells were cultured for an additional 4 days in order to examine the effects of 4-P-PDOT on more mature cells. At the end of the culture period, cells were detached with bleach and bone analog stained with 5% silver nitrate according to manufacturer's instructions to reveal the presence of resorbed bone area (resorption pits). The number of pits and the area of resorbed bone were quantified in 8 microscopic fields in duplicate using Bioquant™ software. Results are presented in FIG. 4. Additional results are presented in FIG. 8.

EXAMPLE 4

Comparison of Effect on Osteoclasts Differentiation and Function in Melatonin and 4-P-PDOT The effect of melatonin on osteoclastogenesis and osteoclast function was assessed with the same methods as those described in Examples 2 and 3 above except that cells were grown in the presence of $10^{-9}$M of melatonin in addition to RANKL. In some experiments, melatonin was added along with $10^{-6}$M of 4-P-PDOT. Cells treated with RANKL alone served as controls. Addition of melatonin did not have a significant effect on osteoclastogenesis (FIGS. 5A and 5B and FIG. 6) but significantly reduced bone resorption (FIG. 7).

EXAMPLE 5

Comparison of cAMP Production Induced by Melatonin and 4-P-PDOT

RAW264.7 cells were grown in culture medium without RANKL until confluence (7 days). Cells were then incubated with $10^{-4}$M of forskolin in presence of various concentrations of melatonin (FIG. 9, panel A), 4-P-PDOT (FIG. 9, panel B) or both (FIG. 9, panel C). Concentrations ranged from $10^{-11}$ to $10^{-5}$M for melatonin and from $10^{-10}$ to $10^{-4}$M for 4-P-PDOT. In the double treatment group, cells were treated with increasing concentrations of melatonin ($10^{-11}$ to $10^{-5}$M) to which $10^{-6}$M of 4-P-PDOT was added. After 30 minutes incubation at 37° C., cells were lysed in TRIS-EDTA buffer supplemented with protease and phosphodiesterase inhibitors at 4° C. The cAMP content was determined in duplicate in 200 µL aliquot of the supernatant using an enzyme immunoassay kit.

FIG. 10 presents normalized cAMP activity values in RAW 264.7 cells treated with melatonin, 4-P-PDOT or melatonin+ 4-P-PDOT wherein in each of panels A, B and C, dose 1 corresponds to the cAMP value for forskolin alone; dose 2 corresponds to $10^{-11}$ of melatonin, $10^{-10}$ 4-P-PDOT, or a combination of $10^{-11}$ of melatonin and $10^{-6}$ 4-P-PDOT, respectively; dose 3 corresponds to $10^{-9}$ of melatonin, $10^{-8}$ 4-P-PDOT, or a combination of $10^{-9}$ of melatonin and $10^{-6}$ 4-P-PDOT, respectively; dose 4 corresponds to $10^{-7}$ of melatonin, $10^{-6}$ 4-P-PDOT, or a combination of $10^{-7}$ of melatonin and $10^{-6}$ 4-P-PDOT, respectively; and dose 5 corresponds to $10^{-5}$ of melatonin, $10^{-4}$ 4-P-PDOT, or a combination of $10^{-5}$ of melatonin and $10^{-6}$ 4-P-PDOT, respectively. cAMP values were normalized against total protein concentration which was determined using the Bradford protein assay.

As may be seen from FIGS. 9 and 10, measurement of cAMP production showed that these cells respond differentially to melatonin and 4-P-PDOT. In the presence of increasing doses of 4-P-PDOT, cAMP production increases while this production is inhibited with melatonin increasing doses.

RAW 264.7 cells then were grown for six days in LabTek™ chamber with RANKL alone or RANKL with melatonin ($10^{-9}$M), melatonin ($10^{-9}$M) and 4-P-PDOT ($10^{-6}$M) or 4-P-PDOT ($10^{-6}$M) alone. Cells were fixed in 3.7% of paraformaldehyde and permeabilized with 0.1% Triton™-X-100. Cells were then incubated in PBS supplemented with 1% bovine albumin (PBSA) for 30 minutes before a 30 minute-incubation with 1:40 anti-phalloidin diluted in PBSA at 37° C. After four rinses in PBS, cells were mounted with a medium containing DAPI and images visualized with 63× objective using a microscope equipped with fluorescence. Images were taken from 10 independent microscopic fields and nuclei counted in multinucleated cells (more than two nuclei). FIG. 13 presents the frequency of number of nucleus as % of total multinucleated.

EXAMPLE 6

Comparison of Apoptosis in Treated and Untreated Cells

RAW264.7 cells were grown in culture medium with RANKL for 6 days with or without $10^{-6}$M of 4-P-PDOT.

Cells were fixed in 3.7% of paraformaldehyde and permeabilized with 0.2% Triton™-X-100. A subset of cells were treated with DNase for 10 minutes at room temperature and served as positive controls. Cell apoptosis was determined using the DeadEnd™ fluorometric TUNEL system. This method measures fragmented DNA through the incorporation of fluorescent-labeled d-UTP. Permeabilized cells were incubated in equilibration buffer with a nucleotide mix and the enzyme that catalyzes the reaction for 1 hour at 37° C. Negative controls were incubated without the enzyme. After several rinses in SSC and PBS, cells were mounted and visualized by fluorescence microscopy. Results are presented in FIG. 11.

EXAMPLE 7

Comparison of Cell Proliferation in Treated and Untreated Cells

After 24 hour attachment, RAW264.7 cells were serum-starved overnight and then grown for 2.5 days in culture medium containing RANKL and melatonin ($10^{-7}$ or $10^{-9}$M), or melatonin ($10^{-9}$M) and a melatonin receptor non-specific antagonist, luzindole ($10^{-8}$M), or melatonin ($10^{-9}$M) and 4-P-PDOT ($10^{-6}$M), or luzindole ($10^{-6}$M), or 4-P-PDOT ($10^{-6}$M) alone. Thymidine incorporation was assayed by the addition of 0.02 µCi/µL of tritiated thymidine to the medium 8 hours before cell harvest. Cells were then washed twice with ice-cold PBS and three times with cold 5% trichloroacetic acid. Cells were lysed in a mixture of 0.5N NaOH and 0.5% SDS and radioactivity of the lysates determined using a beta-counter. Results are presented in FIG. 12.

FIGS. 11 and 12 show that effect of 4-P-PDOT on osteoclast function/bone resorption are not explained by increased apoptosis or by reduced cell proliferation, since these parameters were comparable between 4-P-PDOT-treated vs. untreated cells.

EXAMPLE 8

Expression of Osteoclasts Cells Markers

The effect of melatonin and of 4-P-PDOT on the expression of various genes involved in osteoclast differentiation and activity was evaluated by RT-PCR after 6 days of treatment. FIG. 14 shows that melatonin and 4-P-PDOT induce a significant decrease of RANK's expression on RAW264.7 cell-derived osteoclasts.

EXAMPLE 9

Effect of 4-P-PDOT on Animal Model for Imbalance Between Bone Resorption and Bone Formation 3 week-old male C57Bl/6j mice, which are known to exhibit a very low bone mineral density (BMD) because of a natural mutation limiting the production of melatonin, were injected intraperitoneally with 10 mg/kg of 4-P-PDOT three times a week for 1 month. In parallel, control animals received injections of a solution made of water and ethanol (20%).

During this period, animals were subjected to weekly bone densitometric measurements (BMD and bone mineral content (BMC)) with a PixiMus™ II bone densitometer, and blood and urine collection. Scan of individual spine, long bones (femurs,), were performed. Scans of tibiae, radius and mandible were also performed.

To monitor bone formation rate, 25 mg/kg of tetracycline hydrochloride was injected on days 10 and 20 following the beginning of the injections. Bone histomorphometry for bone formation and resorption static and dynamic parameters were also measured. The biochemical markers used are alkaline phosphatase for bone formation, and urinary deoxypyridinoline for bone resorption.

The first 35 days of the experiments revealed an increase in weight gain, bone mineral accretion at the spine and whole body level in treated mice compared to vehicle-injected animals (see FIGS. 16-18).

The analysis is continued over 12 months. After 6 or 12 months, mice are sacrificed and individual bones and spine scanned by microCT™ (SkyScan CT analyzer) and subsequently fixed and embedded in methylmetacrylate resin to perform histomorphometry analyzes (which include, surface and volume of bone cells: ostoids, osteoblasts, osteocytes, osteoclasts, thickness of cortex and trabeculaes).

The effect of 4-P-PDOT on the formation of bones has also been tested using 4-week old male C57BL/6 mice following weaning. Mice were injected intraperitoneally with 10 mg/kg of 4-P-PDOT three times a week for 4 weeks (28 days). After this period, femur sections were stained to quantify tartrate-resistant acidic phosphatase-(TRAP-) positive osteoclasts (i.e. "active" osteoclasts). FIG. 19 shows that mice treated with 4-P-PDOT have a significant reduction in the number of active osteoclasts as compared to control mice. A Goldner staining was also performed on the femur sections in order to quantify the total number of osteoclasts. As shown in FIG. 20, treatment with 4-P-PDOT also results in an increased in the number of total osteoclasts and in trabecular bone. Also, the results presented in FIG. 21 clearly indicate that mice treated with 4-P-PDOT show a significant reduction (about 3-fold) in the relative number of active osteoclasts in vivo (although the relative number of total osteoclasts is increased) as compared to vehicle-treated mice.

Although the present invention has been described hereinabove by way of specific embodiments thereof, it can be modified, without departing from the spirit and nature of the subject invention as defined in the appended claims.

The invention claimed is:

1. A method comprising: (a) identifying a subject suffering from imbalance between bone resorption and bone formation; and (b) administering to said subject a therapeutically effective amount of (i) 4-phenyl-2-propionamidotetralin (4-P-PDOT); (ii) a conjugate of 4-P-PDOT; (iii) a pharmaceutical acceptable salt of (i) or (ii); or (iv) any combination of (i) to (iii), whereby imbalance between bone resorption and bone formation is improved in said subject.

2. The method of claim 1, wherein the subject suffers from osteoporosis.

3. The method of claim 1, wherein the subject suffers from Paget disease.

4. The method of claim 1, wherein the subject suffers from osteolytic bone cancer.

5. The method of claim 1, wherein the subject suffers from arthritis characterised by the presence of an inflammatory cytokine that induces osteoclasts.

6. The method of claim 1, wherein said administration is a single bolus administration.

7. The method of claim 1, wherein said administration is a daily administration.

8. The method of claim 1, wherein said therapeutically effective amount is between 0.001 and 500 mg/kg of subject/day.

9. The method of claim 1, wherein said improvement of imbalance between bone resorption and bone formation comprises at least one of: an inhibition of bone resorption; an inhibition of osteoclast differentiation; an increase in bone mineral density (BMD); an increase in bone mineral content (BMC); an increase of density of pure cortical bone; an increase of mean density of total bone; an increase of cortical thickness; an increase of pure cortical area assigned to be cortical; an increase of tibial diaphyseal total bone areas; an increase of mineralization apposition rate; an increase of bone formation rate/bone surface referent; an increase of mineralizing surface for endocortical or periosteal surface; a decrease of serum alkaline phosphatase; a decrease of intra-cortical regions of hypo-mineralized osteoid; a decrease of osteoid thickness and a decrease of osteoid condensation.

10. The method of claim 1, wherein said correction of imbalance between bone resorption and bone formation comprises an inhibition of bone resorption.

11. The method of claim 1, wherein said correction of imbalance between bone resorption and bone formation comprises an inhibition of osteoclast differentiation.

12. The method of claim 1, wherein said correction of imbalance between bone resorption and bone formation comprises an increase in bone mineral density (BMD).

13. The method of claim 1, wherein said correction of imbalance between bone resorption and bone formation comprises an increase in bone mineral content (BMC).

14. The method of claim 1, which further comprises the administration of another agent selected from the group consisting of a bisphosphonate, raloxifene, nasal calcitonin and teriparatide.

15. The method of claim 1, wherein the subject is a human.

* * * * *

UNITED STATES PATENT AND TRADEMARK OFFICE
CERTIFICATE OF CORRECTION

PATENT NO. : 8,129,432 B2  Page 1 of 1
APPLICATION NO. : 12/526311
DATED : March 6, 2012
INVENTOR(S) : Moreau and Mailhot It is certified that error appears in the above-identified patent and that said Letters Patent is hereby corrected as shown below:

In the Specification:

Column 1, line 34, "$14033\_{33}$—sequence listing$\_{ST}{}^{25}$," should read --14033_33 – sequence listing_ST25,--.

Column 1, line 35, "2Ko." should read --2Kb.--.

Column 3, line 11, "4-P-PDOT);" should read --4-P-PDOT;--.

Column 5, line 37, "inhibit inhibiting" should read --inhibit--.

Column 6, lines 49-50, "prevent, delay or correct" should read --prevents, delays or corrects--.

Column 8, line 15, "Press), in" should read --Press). In--.

Column 10, line 24, "animal" should read --animals--.

Column 14, line 9, "Scan" should read --Scans--.

In the Claims:

Column 16, line 47, claim 10, "correction" should read --improvement--.

Column 16, line 50, claim 11, "correction" should read --improvement--.

Column 16, line 53, claim 12, "correction" should read --improvement--.

Column 16, line 56, claim 13, "correction" should read --improvement--.

Signed and Sealed this
Twenty-second Day of April, 2014

Michelle K. Lee
*Deputy Director of the United States Patent and Trademark Office*